US010179775B2

(12) United States Patent
Hilderbrand et al.

(10) Patent No.: US 10,179,775 B2
(45) Date of Patent: Jan. 15, 2019

(54) CYCLOOCTENES FOR BIOORTHOGONOL REACTIONS

(71) Applicant: The General Hospital Corporation, Boston, MA (US)

(72) Inventors: Scott A. Hilderbrand, Swampscott, MA (US); Balazs R. Varga, Komarno (SK); Ralph Weissleder, Peabody, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/502,806

(22) PCT Filed: Aug. 11, 2015

(86) PCT No.: PCT/US2015/044655
§ 371 (c)(1),
(2) Date: Feb. 9, 2017

(87) PCT Pub. No.: WO2016/025480
PCT Pub. Date: Feb. 18, 2016

(65) Prior Publication Data
US 2017/0233365 A1     Aug. 17, 2017

Related U.S. Application Data

(60) Provisional application No. 62/039,653, filed on Aug. 20, 2014, provisional application No. 62/035,540, filed on Aug. 11, 2014.

(51) Int. Cl.
*C07D 321/12* (2006.01)
*C07D 405/12* (2006.01)
*C07C 43/196* (2006.01)
*C07D 413/12* (2006.01)
*C07D 263/52* (2006.01)
*C07D 207/46* (2006.01)

(52) U.S. Cl.
CPC .......... *C07D 321/12* (2013.01); *C07C 43/196* (2013.01); *C07D 207/46* (2013.01); *C07D 263/52* (2013.01); *C07D 405/12* (2013.01); *C07D 413/12* (2013.01); *C07C 2601/18* (2017.05)

(58) Field of Classification Search
CPC .... C07D 321/12; C07D 405/12; C07C 43/196
See application file for complete search history.

(56) References Cited

U.S. PATENT DOCUMENTS

| | | | |
|---|---|---|---|
| 4,522,811 A | 6/1985 | Eppstein et al. | |
| 5,208,020 A | 5/1993 | Chari et al. | |
| 5,475,092 A | 12/1995 | Chari et al. | |
| 5,585,499 A | 12/1996 | Chari et al. | |
| 5,846,545 A | 12/1998 | Chari et al. | |
| 6,468,798 B1 | 10/2002 | Debs et al. | |
| 6,471,996 B1 | 10/2002 | Sokoll et al. | |
| 6,472,375 B1 | 10/2002 | Hoon et al. | |
| 2009/0023916 A1 | 1/2009 | Fox et al. | |
| 2011/0268654 A1 | 11/2011 | Hilderbrand et al. | |
| 2012/0034161 A1 | 2/2012 | Robillard et al. | |
| 2012/0039803 A1 | 2/2012 | Robillard et al. | |
| 2013/0189184 A1 | 7/2013 | Lub et al. | |
| 2013/0266512 A1 | 10/2013 | Fox et al. | |
| 2013/0272959 A1 | 10/2013 | Rossin et al. | |
| 2013/0302246 A1 | 11/2013 | Hilderbrand et al. | |
| 2013/0309170 A1 | 11/2013 | Reiner et al. | |
| 2014/0073764 A1 | 3/2014 | Lemke et al. | |
| 2014/0093450 A1 | 4/2014 | Robillard et al. | |
| 2014/0093522 A1 | 4/2014 | Robillard et al. | |
| 2014/0199331 A1 | 7/2014 | Robillard et al. | |

OTHER PUBLICATIONS

International Search Report and Written Opinion dated Dec. 30, 2015 in international No. PCT/US2015/044655, 15 pgs.
Thermo Scientific Crosslinking Technical Handbook—easy molecular bonding crosslinking technology, 2012, 56 pages.
'www.thermofisher.com' [online]. Amine-Reactive Crosslinker, Aug. 25, 2015 [retrieved on Oct. 24, 2017] Retrieved from the Internet: URL <https://www.thermofisher.com/us/en/home/life-science/protein-biology/protein-biology-learning-center/protein-biology-resource-library/pierce-protein-methods/amine-reactive-crosslinker-chemistry.html>. 8 pages.
Blackman et al., "The Tetrazine Ligation: Fast Bioconjugation based on Inverseelectron-demand Diels-Alder Reactivity," J. Am. Chem. Soc., Oct. 2008, 130: 13518-13519.
Brannock and Lappin, "Preparation and Properties of 1,3-Dioxep-5-enes," J. Org. Chem, Dec. 1956, 1366-1368.
Dalpozzo et al., "Erbium(III) Triflate is a Highly Efficient Catalyst for the Synthesis of β-Alkoxy Alcohols, 1,2-Diols and β-Hydroxy Sulfides by Ring Opening of Epoxides," Synthesis, 2009, 20: 3433-3438.
Devaraj and Weissleder, "Biomedical Applications of Tetrazine Cycloadditions," Acc. Chem. Res., Sep. 2011, 44: 816-827.
Devaraj et al., "Tetrazine-Based Cycloadditions: Application to Pretargeted Live Cell Imaging," Bioconjugate Chem., 2008, 19: 2297-2299.
Fedorenko et al., "Facial selectivity in the reaction of dihalocarbenes with 2-substituted 4, 7-dihydro-1, 3-dioxepines," Mendeleev Commun., 2007, 17: 170-171.
International Preliminary Report on Patentability in International Application No. PCT/US2015/044655, dated Feb. 14, 2017, 7 pages.
Jendralla, "(5RS, 7RS)-7-Methoxy-1,3-dioxacyclooct-5(E)-en Synthese eines stabilen Bishetero-trans-cyclooctens; ein neues heterocyclisches System," H. Chem. Ber., Jan. 1982, 115: 201-209 (with English abstract).
Keliher et al., "High-Yielding, Two-Step 18 F Labeling Strategy for 18F-PARP1 Inhibitors," ChemMedChem, Mar. 2011, 6: 424-427.
Menear et al., "4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1," J. Med. Chem., Oct. 2008, 51: 6581-6591.

(Continued)

*Primary Examiner* — Shawquia Jackson
(74) *Attorney, Agent, or Firm* — Fish & Richardson P.C.

(57) ABSTRACT

This disclosure relates to trans-cyclooctene compounds and methods of using the same in bioorthogonal labeling experiments.

24 Claims, 1 Drawing Sheet

(56) References Cited

OTHER PUBLICATIONS

Nguyen and Francis, "Practical Synthetic Route to Functionalized Rhodamine Dyes," Org. Lett., 2003, 5: 3245-3248.
Rossin et al., "Highly reactive trans-cyclooctene tags with improved stability for Diels-Alder chemistry in living systems," Bioconjugate Chem., Jul. 2013, 24: 1210-1217.
Rossin et al., "In vivo chemistry for pretargeted tumor imaging in live mice," Angew. Chem. Int. Ed., Apr. 2010, 49: 3375-3378.
Scyferth et al., "Halomcthyl-Metalcompounds. Lxxii*. The Preparation of A-Halocyclopropyl Derivatives of Lithium and Their Application in The Synthesis of O:-Halocyclopropyl Compounds of Silicon, Germanium, Tin, Lead, and Mercury. A Novel Isomerization of Syn-7-Bromoanti-7-Lithionorcarane to The Anti-7-Bromo-Syn-7-Lithio Isomer," J Orgmet. Chem, 1975, 88: 255-286.
Womack et al., "Ethyl Diazoacetate," Org. Synth., 1955, 3:392.
Wu and Senter, "Arming antibodies: prospects and challenges for immunoconjugates," Nat. Biotechnol., 2005, 23:1137-1146.
Yang et al., "Bioorthogonal imaging of aurora kinase A in live cells," Angew. Chem. Int. Ed., Jul. 2012, 51: 6598-6603.

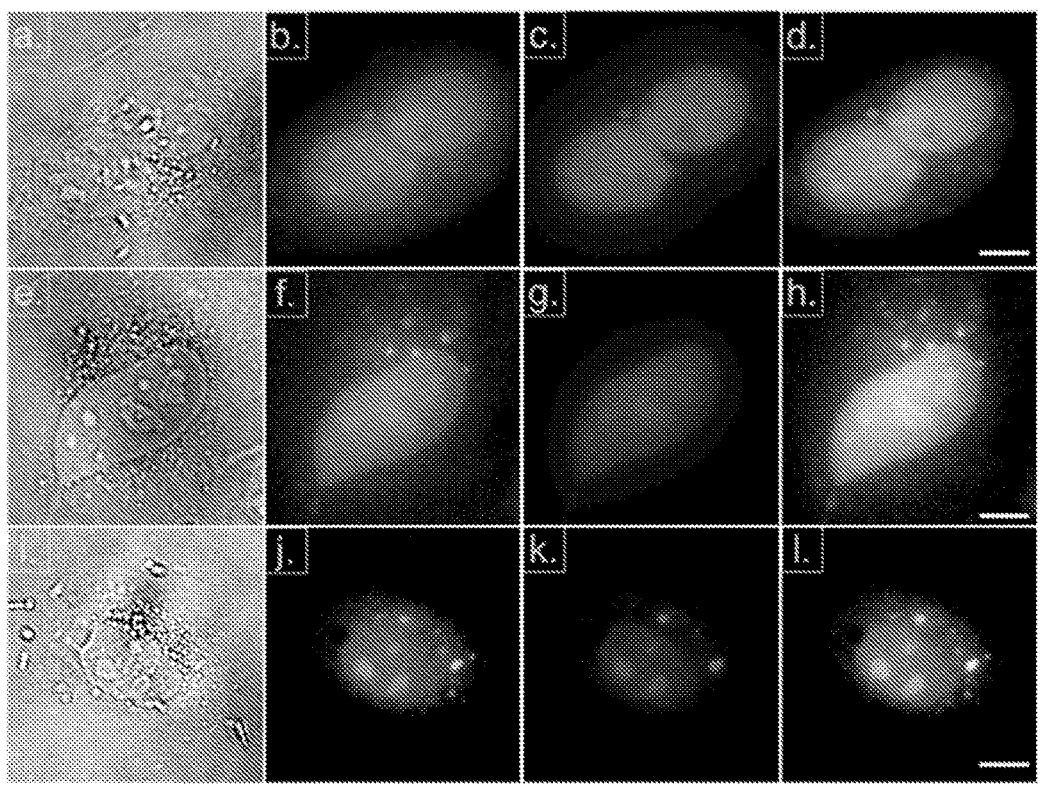

CYCLOOCTENES FOR BIOORTHOGONOL REACTIONS

CROSS-REFERENCE TO RELATED APPLICATIONS

This application is a § 371 National Stage Application of PCT/US2015/044655, filed Aug. 11, 2015, which claims priority to U.S. Application Ser. Nos. 62/035,540, filed on Aug. 11, 2014, and 62/039,653, filed on Aug. 20, 2014, all of which are incorporated by reference in their entireties.

TECHNICAL FIELD

This disclosure relates to trans-cyclooctene compounds and methods of using the same in bioorthogonal labeling experiments.

BACKGROUND

The introduction of the tetrazine-based inverse electron demand Diels-Alder (iEDDA) reaction was a major breakthrough in bioorthogonal chemistry (see, e.g., Blackman, M. L. et al., *J. Am. Chem. Soc.* 2008, 130, 13518-13519; and Devaraj, N. K. et al., *Bioconjugate Chem.* 2008, 19, 2297-2299). The stability of the reaction partners and the excellent kinetics, in particular when employing trans-cyclooctene as the dienophile, has made these reagents a useful tool for bioorthogonal labeling experiments (see, e.g., Blackman, M. L. et al., *J. Am. Chem. Soc.* 2008, 130, 13518-13519; and Devaraj, N. K. et al., *Bioconjugate Chem.* 2008, 19, 2297-2299; Rossin, R. et al., *Angew. Chem. Int. Ed.* 2010, 49, 3375-3378; Devaraj, N. K. and Weissleder, R. *Acc. Chem. Res.* 2011, 44, 816-827; and Keliher, E. et al., *ChemMedChem* 2011, 6, 424-427). Early research on this cycloaddition chemistry focused on optimization of the cycloaddition reaction kinetics via modification of tetrazine. More recently, additional trans-cyclooctene derivatives with significantly improved cycloaddition kinetics have been reported (see, e.g., Blackman, M. L. et al., *J. Am. Chem. Soc.* 2008, 130, 13518-13519; and Devaraj, N. K. et al., *Bioconjugate Chem.* 2008, 19, 2297-2299), but at the expense of decreased chemical stability or significantly increased molecular weight of the reactants.

SUMMARY

Provided herein are trans-cyclooctene compounds which can have increased hydrophilicity, reactivity, and/or stability in aqueous solution while maintaining the small size of the trans-cyclooctene (TCO) which can help minimize the potential for interference with any small molecule targets to which the TCO could be conjugated to.

In some embodiments, a trans-cyclooctene compound provided herein can be a compound of Formula I:

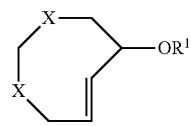

or a pharmaceutically acceptable salt thereof, wherein:
each X is independently $CH_2$ or O;
$R^1$ is $-(CH_2-CH_2-O)_nR^2$;
$R^2$ is selected from the group consisting of H, $C_{1-6}$alkyl, an amine-reactive crosslinking group; and
n is an integer from 1 to 20.

In some embodiments, a compound of Formula I can be a compound of Formula IA:

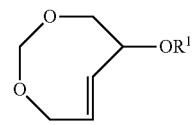

or a pharmaceutically acceptable salt thereof,
wherein:
$R^1$ is $-(CH_2-CH_2-O)_nR^2$;
$R^2$ is selected from the group consisting of H, $C_{1-6}$alkyl, or an amine-reactive crosslinking group; and
n is an integer from 1 to 20.

In some embodiments, $R^2$ is selected from H and $C_{1-6}$alkyl. In some embodiments, $R^2$ is an amine-reactive crosslinking group. For example, $R^2$ is can be an NHS carbamate such as N,N'-disuccinimidyl carbonate.

In some embodiments, n is 1.

Non-limiting compounds of Formula I and/or Formula IA include:

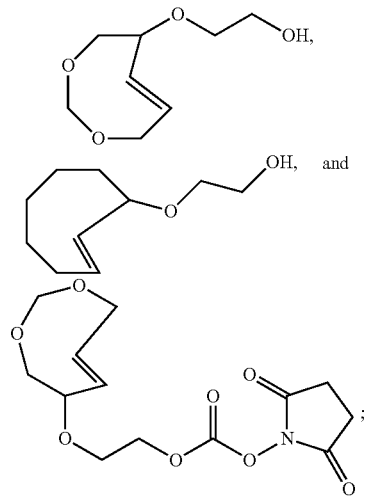

or a pharmaceutically acceptable salt thereof.

Also provided herein are compounds of Formula II:

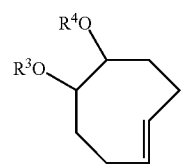

or a pharmaceutically acceptable salt thereof, wherein:

$R^3$ is selected from the group consisting of H, $C_{1-6}$alkyl, and —$(CH_2—CH_2—O)_nR^5$;

$R^4$ is selected from the group consisting of H, $C_{1-6}$alkyl, and —$(CH_2—CH_2—O)_nR^5$;

wherein one of $R^3$ and $R^4$ is —$(CH_2—CH_2—O)_nR^5$;

$R^5$ is selected from the group consisting of H, $C_{1-6}$alkyl, and an amine-reactive crosslinking group; and n is an integer from 1 to 20.

In some embodiments, $R^3$ is H.

In some embodiments, $R^5$ is a $C_{1-6}$ alkyl. In some embodiments, $R^5$ is an amine-reactive crosslinking group. For example, $R^5$ is can be an NHS carbamate such as N,N'-disuccinimidyl carbonate.

In some embodiments, n is 3.

Exemplary compounds of Formula II are selected from the group consisting of:

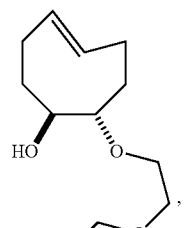

,

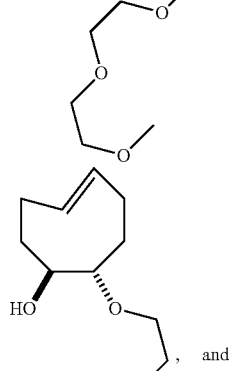

, and

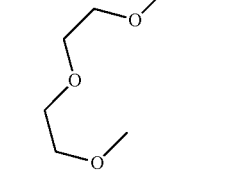

;

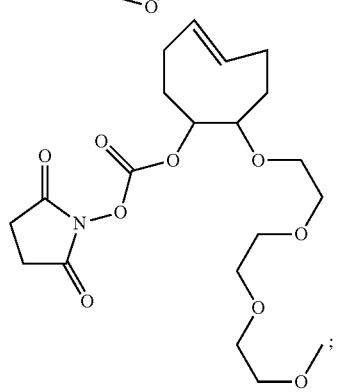

or a pharmaceutically acceptable salt thereof.

Further provided herein are compounds of Formula III:

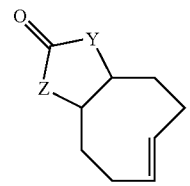

or a pharmaceutically acceptable salt thereof, wherein:

Y is O or $NR^6$;

Z is O or $NR^6$;

wherein one of Y and Z is O, and the other is $NR^6$;

$R^6$ is —$(CH_2)_m$—$(CH_2—CH_2—O)_nR^7$;

$R^7$ is selected from the group consisting of H, $C_{1-6}$alkyl, and an amine-reactive crosslinking group;

m is an integer from 1 to 20; and n is an integer from 1 to 20.

In some embodiments, $R^7$ is H. In some embodiments, $R^7$ is an amine-reactive crosslinking group. For example, $R^7$ is can be an NHS carbamate such as N,N'-disuccinimidyl carbonate.

In some embodiments, n is 1.

In some embodiments, m is 2.

Non-limiting examples of a compound of Formula III include:

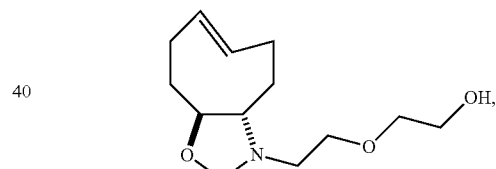

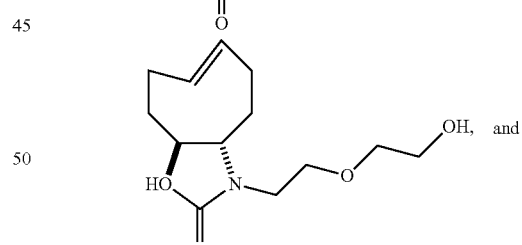

, and

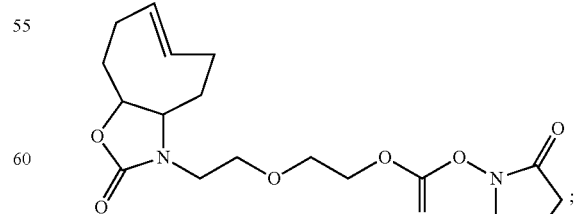
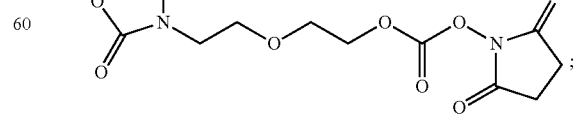

;

In some embodiments, the compound of Formula III is selected from the group consisting of:

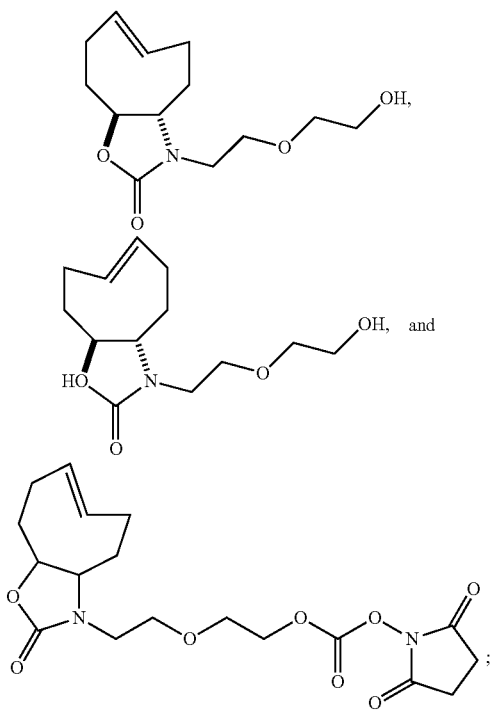

or a pharmaceutically acceptable salt thereof.

The invention provides several advantages. For example, the trans-cyclooctene compounds provided herein display significantly improved hydrophilicity and/or improved or equivalent kinetics compared to previously prepared trans-cyclooctene compounds. In addition, in some cases, the compounds provided herein exhibited stability in aqueous solution and in the presence of thiols such as cysteine and mercaptoethanol.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DESCRIPTION OF DRAWINGS

FIG. 1 illustrates bioorthogonal imaging of PARP protein in HT1080 cells. HT1080 cells (expressing PARP1 fused to mCherry) were treated with 5 μM compound 45 (a-d), 46 (e-h) and 47 (i-l) for 30 minutes. After washing with growth media three times for 5 minutes each, cells were incubated for 30 minutes with 1 μM of CFDA-Tz for bio-orthogonal reaction inside the live cells. Following fixation, 40× images were collected by deconvolution microscopy a, e, i) bright field images; b, f, j) Olaparib-TCO/Tz-CFDA staining; c, g, k) PARP1-mCherry, d, h, l) merged images. Scale bar: 10 μm.

DETAILED DESCRIPTION

One issue encountered in the application of the chemistry of tetrazine-based inverse electron demand Diels-Aldder (iEDDA) is the high lipophilicity of trans-cyclooctenol (TCO-OH), an eight membered carbon ring structure, lacking any other polar substituents than the OH used for conjugation. Lipophilicity increases the potential for undesired nonspecific binding of the reagents during biological imaging experiments.

Provided herein are trans-cyclooctene compounds which can have increased hydrophilicity and/or reactivity while maintaining the small size of the trans-cyclooctene (TCO) which can help minimize the potential for interference with any small molecule targets to which the TCO could be conjugated to.

Compounds

In some embodiments, a trans-cyclooctene compound provided herein can be a compound of Formula I:

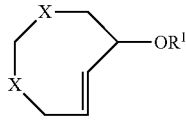

or a pharmaceutically acceptable salt thereof,
wherein:
each X is independently $CH_2$ or O;
$R^1$ is $-(CH_2-CH_2-O)_nR^2$;
$R^2$ is selected from the group consisting of H, $C_{1-6}$alkyl, an NHS ester, and an imidoester; and
n is an integer from 1 to 20.

In some embodiments, a compound of Formula I can be a compound of Formula IA:

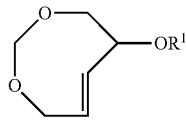

or a pharmaceutically acceptable salt thereof,
wherein:
$R^1$ is $-(CH_2-CH_2-O)_nR^2$;
$R^2$ is selected from the group consisting of H, $C_{1-6}$alkyl, or an amine-reactive crosslinking group; and
n is an integer from 1 to 20.

In some embodiments, $R^2$ is selected from H and $C_{1-6}$alkyl. In some embodiments, $R^2$ can be an amine-reactive crosslinking group. Such groups can be used to increase the reactivity of the compounds provided herein with primary amines (e.g., primary amines provided on diene compounds, polypeptides, and in the side chain of lysine residues). Exemplary crosslinking groups include isothiocyanates, isocyanates, acyl azides, NHS esters (e.g., NHS carbamates), sulfonyl chlorides, aldehydes, glyoxals, epoxides, oxiranes, carbonates, aryl halides, imidoesters, carbodiimides, anhydrides, hydrazines, hydrazides, hydroxyl amines, and fluorophenyl esters. In some embodiments, the amine-reactive crosslinking group can conjugate to an amine via either acylation or alkylation. In some embodiments, the amine-reactive crosslinking group is an NHS carbamate such as N,N'-disuccinimidyl carbonate.

In some embodiments, n is an integer from 1 to 20 (e.g., 1 to 18, 1 to 16, 1 to 14, 1 to 12, 1 to 10, 1 to 8, 1 to 6, 1 to 4, 1 to 3, 2 to 20, 4 to 20, 5 to 20, 8 to 20, 10 to 20, 15 to 20, 16 to 20, 2 to 18, 5 to 15, 6 to 12, 8 to 16, 2 to 6, and 2 to 10). In some embodiments, n is 1.

Non-limiting compounds of Formula I and/or Formula IA include:

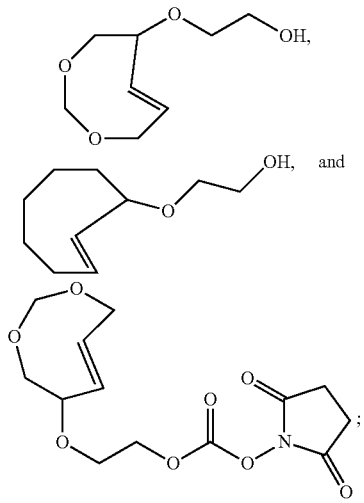

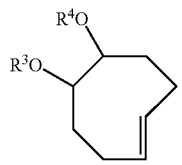

or a pharmaceutically acceptable salt thereof.

Also provided herein are compounds of Formula II:

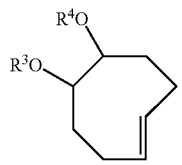

or a pharmaceutically acceptable salt thereof, wherein:

$R^3$ is selected from the group consisting of H, $C_{1-6}$alkyl, and $-(CH_2-CH_2-O)_nR^5$;

$R^4$ is selected from the group consisting of H, $C_{1-6}$alkyl, and $-(CH_2-CH_2-O)_nR^5$;

wherein one of $R^3$ and $R^4$ is $-(CH_2-CH_2-O)_nR^5$;

$R^5$ is selected from the group consisting of H, $C_{1-6}$alkyl, and an amine-reactive crosslinking group; and n is an integer from 1 to 20.

In some embodiments, $R^3$ is H.

In some embodiments, $R^5$ is a $C_{1-6}$ alkyl. In some embodiments, $R^5$ can be an amine-reactive crosslinking group. Such groups can be used to increase the reactivity of the compounds provided herein with primary amines (e.g., primary amines provided on diene compounds, polypeptides, and in the side chain of lysine residues). Exemplary crosslinking groups include isothiocyanates, isocyanates, acyl azides, NHS esters (e.g., NHS carbamates), sulfonyl chlorides, aldehydes, glyoxals, epoxides, oxiranes, carbonates, aryl halides, imidoesters, carbodiimides, anhydrides, hydrazines, hydrazides, hydroxyl amines, and fluorophenyl esters. In some embodiments, the amine-reactive crosslinking group can conjugate to an amine via either acylation or alkylation. In some embodiments, the amine-reactive crosslinking group is an NHS carbamate such as N,N'-disuccinimidyl carbonate.

In some embodiments, n is an integer from 1 to 20 (e.g., 1 to 18, 1 to 16, 1 to 14, 1 to 12, 1 to 10, 1 to 8, 1 to 6, 1 to 4, 1 to 3, 2 to 20, 4 to 20, 5 to 20, 8 to 20, 10 to 20, 15 to 20, 16 to 20, 2 to 18, 5 to 15, 6 to 12, 8 to 16, 2 to 6, and 2 to 10). In some embodiments, n is 3.

Exemplary compounds of Formula II are selected from the group consisting of:

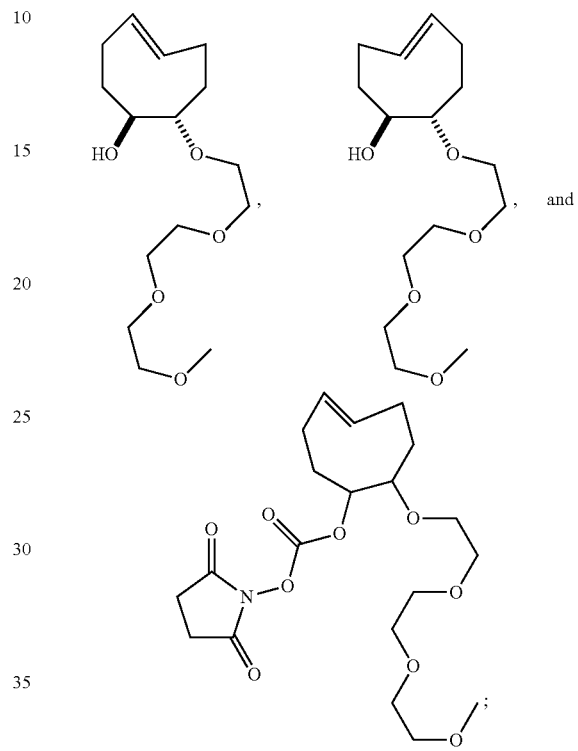

or a pharmaceutically acceptable salt thereof.

Further provided herein are compounds of Formula III:

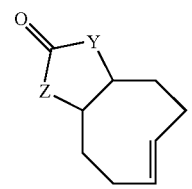

or a pharmaceutically acceptable salt thereof, wherein:

Y is O or $NR^6$;

Z is O or $NR^6$;

wherein one of Y and Z is O, and the other is $NR^6$;

$R^6$ is $-(CH_2)_m-(CH_2-CH_2-O)_nR^7$;

$R^7$ is selected from the group consisting of H, $C_{1-6}$alkyl, and an amine-reactive crosslinking group;

m is an integer from 1 to 20; and n is an integer from 1 to 20.

In some embodiments, $R^7$ is H. In some embodiments, $R^5$ can be an amine-reactive crosslinking group. Such groups can be used to increase the reactivity of the compounds provided herein with primary amines (e.g., primary amines provided on diene compounds, polypeptides, and in the side chain of lysine residues). Exemplary crosslinking groups include isothiocyanates, isocyanates, acyl azides, NHS esters (e.g., NHS carbamates), sulfonyl chlorides, aldehydes, glyoxals, epoxides, oxiranes, carbonates, aryl halides, imidoesters, carbodiimides, anhydrides, hydrazines, hydrazides, hydroxyl amines, and fluorophenyl esters. In some embodiments, the amine-reactive crosslinking group can conjugate to an amine via either acylation or alkylation. In some embodiments, the amine-reactive crosslinking group is an NHS carbamate such as N,N'-disuccinimidyl carbonate.

In some embodiments, n is an integer from 1 to 20 (e.g., 1 to 18, 1 to 16, 1 to 14, 1 to 12, 1 to 10, 1 to 8, 1 to 6, 1 to 4, 1 to 3, 2 to 20, 4 to 20, 5 to 20, 8 to 20, 10 to 20, 15 to 20, 16 to 20, 2 to 18, 5 to 15, 6 to 12, 8 to 16, 2 to 6, and 2 to 10). In some embodiments, n is 1.

In some embodiments, m is an integer from 1 to 20 (e.g., 1 to 18, 1 to 16, 1 to 14, 1 to 12, 1 to 10, 1 to 8, 1 to 6, 1 to 4, 1 to 3, 2 to 20, 4 to 20, 5 to 20, 8 to 20, 10 to 20, 15 to 20, 16 to 20, 2 to 18, 5 to 15, 6 to 12, 8 to 16, 2 to 6, and 2 to 10). In some embodiments, m is 2.

Non-limiting examples of a compound of Formula III include:

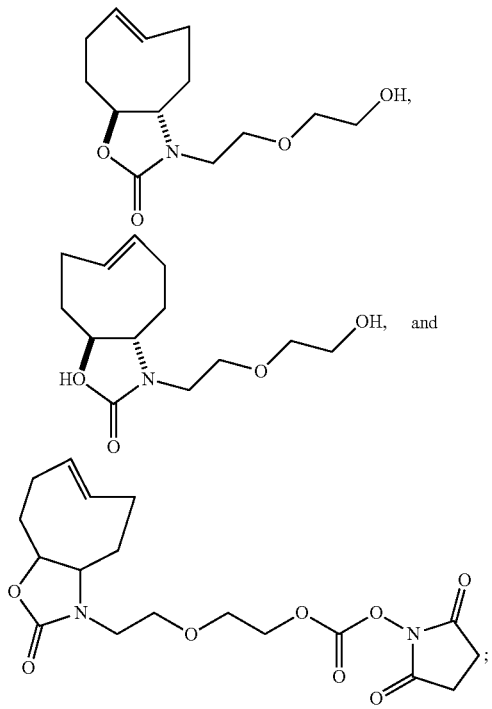

In some embodiments, the compound of Formula III is selected from the group consisting of:

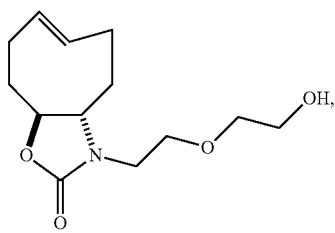

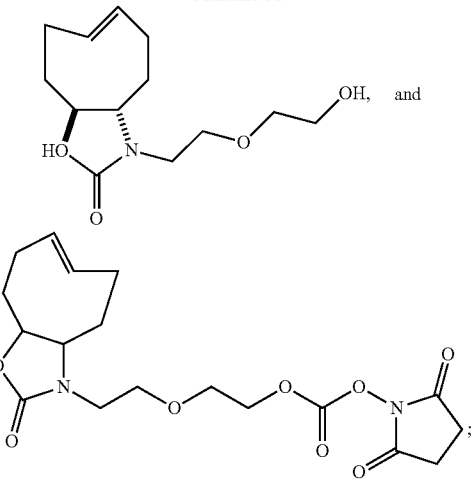

or a pharmaceutically acceptable salt thereof.

The invention provides several advantages. For example, the trans-cyclooctene compounds provided herein display significantly improved hydrophilicity and/or improved or equivalent kinetics compared to previously prepared trans-cyclooctene compounds. In addition, in some cases, the compounds provided herein exhibited stability in aqueous solution and in the presence of thiols such as cysteine and mercaptoethanol.

The compounds provided herein can be prepared using methods such as those described in the Examples.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. Conventional methods for preparing salt forms are described, for example, in *Handbook of Pharmaceutical Salts: Properties, Selection, and Use,* Wiley-VCH, 2002.

The skilled artisan will recognize that some structures described herein can be resonance forms or tautomers of compounds that can be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

Methods of Use

Bioconjugation methods using inverse electron demand Diels-Alder cycloadditions between tetrazines and highly strained dienophiles such trans-cyclooctene are known, however the trans-cyclooctene has limited solubility stability in aqueous media. The compounds provided herein exhibit one or more of increased hydrophilicity, reactivity, and stability in aqueous media.

In some embodiments, the bioorthogonal inverse electron demand Diels-Alder (iEDDA) reaction can be tailored to provide a straightforward method for the rapid, specific covalent labeling and imaging inside living cells using ligands such as small molecules and other biomolecules. For example, tetrazine-linked fluorescent probes that can react rapidly via an iEDDA reaction with strained dienophiles such as those provided herein can be used to image cells. In some embodiments, such methods can be used to label and image a ligand bound to a specific target. For example, this bioorthogonal inverse electron demand Diels-Alder reaction can be applied to an fluorophoric tetrazine derivative conjugated to a PAROP1 inhibitor (AZD2281), which is physically coupled to a compound provided herein (see Example 6) and can be used to label and image PARP1 in cells.

In some embodiments, a ligand, e.g., an antibody, small molecule or other biomolecule, can be physically attached to a compound as provided herein. In some embodiments, the ligand carries a functional group such as an amine, alcohol, carboxylic acid or ester, or other group of atoms on the ligand that can undergo a chemical reaction allowing attachment to a compound provided herein. Alternatively or in addition, a compound provided herein can possess a reactive functional group for attachment to the ligand. Thus, the reactive functional group on the ligand and/or dienophile undergoes a chemical reaction to form a link between the two.

Dienes useful in the present disclosure include but are not limited to aromatic ring systems that contain two adjacent nitrogen atoms, for example, tetrazines, pyridazines, substituted or unsubstituted 1,2-diazines. Other 1,2-diazines can include 1,2-diazines annelated to a second π-electron-deficient aromatic ring such as pyrido[3,4-d]pyridazines, pyridazino[4,5-d]pyridazines, and 1,2,4-triazines. Pyridazines can also be fused with a five-membered heterocycle such as imidazo[4,5-d]pyridazines and 1,2,3-triazolo[4,5-d]pyridazines. In some embodiments, the diene is an asymmetrical tetrazine as described in U.S. Publication Nos. 2013/0302246; 2011/0268654; 2013/0266512; 2009/0023916; 2014/0199331; 2014/0093522; 2014/0093450; 2013/0272959; 2013/0189184; 2012/0039803; and 2012/0034161.

Dienophiles useful in the methods described herein include compounds of Formula I, II, and/or III, or a pharmaceutically acceptable salt thereof.

The methods and compositions described herein can also be useful for delivering a payload to a biological target. The payload can be used, e.g., for labeling (e.g., a detectable agent such as a fluorophore), or for therapeutic purposes (e.g., a cytotoxin or other therapeutic agent).

In some embodiments the payload is a therapeutic agent such as a cytotoxin, radioactive ion, or other therapeutic agents. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Radioactive ions include, but are not limited to iodine (e.g., iodine 125 or iodine 131), strontium 89, phosphorous, palladium, cesium, iridium, phosphate, cobalt, yttrium 90, Samarium 153 and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Nucleic acids, e.g., inhibitory nucleic acids, e.g., small interfering RNAs, antisense, aptamers, can also be used as therapeutic agents.

Examples of detectable substances include various organic small molecules, inorganic compounds, nanoparticles, enzymes or enzyme substrates, fluorescent materials, luminescent materials, bioluminescent materials, chemiluminescent materials, radioactive materials, and contrast agents. Examples of suitable enzymes include horseradish peroxidase, alkaline phosphatase, beta-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-4-bora-3a,4a-diaza-s-indacene-3-yl)styryloxy)acetyl) aminohexanoic acid, succinimidyl ester (BODIPY® 650/665-X), 7-N,N-diethylaminocoumarin, VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{18}F$, $^{67}Ga$, $^{81m}Kr$, $^{82}Rb$, $^{111}In$, $^{123}I$, $^{133}Sc$, $^{201}Tl$, $^{125}I$, $^{35}S$, $^{14}C$, or $^{3}H$, $^{99m}Tc$ (e.g., as pertechnetate (technetate(VII), $TcO_4^-$) either directly or indirectly, or other radioisotope detectable by direct counting of radioemission or by scintillation counting.

In addition, contrast agents, e.g., contrast agents for MRI or NMR, for X-ray CT, Raman imaging, optical coherence tomogrpahy, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons can also be used.

In some embodiments, the detectable agent is a non-detectable pre-cursor that becomes detectable upon activation. Examples include fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE (VisEn Medical))

The compounds, compositions, and methods described herein can be used in a number of different scenarios in which delivery of a substance (the "payload") to a biological target is desired, for example delivery of detectable substances for detection of the target, or delivery of a therapeutic agent. Detection methods can include both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

As one example, the Diels-Alder coupling reaction as described herein can be used in place of standard avidin (or streptavidin)/biotin coupling procedures. Many tissue types may contain endogenous biotin, so with the current standard biotin-based coupling procedures, an additional step to block the activity of the endogenous biotin may be necessary to eliminate unwanted non-specific background staining. This blocking step is not necessary if the compositions described herein are used.

This procedure is also used for electron microscopy where the fluorophore-dienophile (or -diene) component is replaced by a gold nanoparticle-dienophile (or -diene) conjugate.

The Diels-Alder coupling compositions described herein should also be applicable to any in situ hybridization (ISH) or fluorescence in situ hybridization (FISH) protocol for visualization of DNA or RNA in tissue or cell preparations in which the avidin (streptavidin)/biotin system is employed, e.g., Tyramide Signal Amplification FISH.

The Diels-Alder coupling reaction as described herein can also be used as an alternative to secondary antibodies or in place of standard avidin (or streptavidin)/biotin coupling procedures during a western blot.

In addition, the compositions described herein can be used to deliver therapeutic agents to cells or tissues, e.g., in living animals. Thus a therapeutic compound is attached to one half of the Diels-Alder pair, and a ligand that targets the desired cell or tissue is attached to the other half For example, a ligand such as an antibody that recognizes a tumor cell is attached to one half, and the other half is linked to a payload comprising a cytotoxin, e.g., a toxin or radioactive substance.

These compositions are particularly useful for pretargeting strategies where the ligand has a long half life in the body. For example, monoclonal antibodies have a very long half-life in the blood. This property leads to poor target-to-background ratios when the antibodies are labeled directly with imaging agents or cytotoxins. See, e.g., Wu and Senter, Nat. Biotechnol. 23:1137-1146 (2005). The methods, compounds, and compositions described herein can circumvent these problems.

Pharmaceutical Compositions and Methods of Administration

The methods described herein include the manufacture and use of pharmaceutical compositions, which include compounds described herein as active ingredients. Also included are the pharmaceutical compositions themselves. In some embodiments, the compositions include a compound provided herein or a bioorthogonal conjugate thereof.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Definitions

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups will comprise 1 to 6 carbon atoms (for example, 1 to 4 carbon atoms or 1 to 2 carbon atoms).

The term "substituted" refers to moieties having substituents replacing a hydrogen on one or more non-hydrogen atoms of the molecule. It will be understood that "substitution" or "substituted with" means that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, an alkyl, a halide, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an arylalkyl, a heteroarylalkyl, an aryl, or heteroaryl moiety.

EXAMPLES

The invention is further described in the following examples, which do not limit the scope of the invention described in the claims.

General Methods

Unless otherwise noted, all reactions and manipulations were performed in dry glassware under air at ambient temperature. NMR spectra were recorded using a 600 MHz Varian VNMRS spectrometer, a Varian 500 MHz, a Bruker 400 MHz or a Bruker 250 MHz spectrometer. $^1$H or $^{13}$C NMR chemical shifts are reported vs. Me$_4$Si and were determined by reference to the residual $^1$H or $^{13}$C solvent peaks. Splitting patterns are designated as s (singlet), d (doublet), t (triplet), q (quadruplet), m (multiplet), dd (doublet of a doublets), dt (doublet of triplets), td (triplet of doublets) and dq (doublet of quadruplets).

The high-resolution electrospray ionization (ESI) mass spectra were obtained on a Bruker Daltonics APEXIV 4.7 Tesla Fourier Transform mass spectrometer (FT-ICR-MS) in the Department of Chemistry Instrumentation Facility at the Massachusetts Institute of Technology.

Unless otherwise noted, reagents were from commercial suppliers, notably Sigma-Aldrich, Fisher Scientific, Acros Organics, TCI America, Chem-Impex, Oakwood Chemical and Crescent Chemicals. Ethylene glycol was dried over 4 Å molecular sieves as an approximately 20 vol % solution in DCM/MeOH 4:1. It was considered sufficiently dry when the water content was less than 5 mol % as determined by $^1$H NMR. If necessary, multiple batches of dry molecular sieves were used to achieve the desired level of dryness. The photochemical reactions were performed in a Rayonet PRP-100 system. Microwave experiments were performed in a CEM Discover system. Analytical thin-layer chromatography (TLC) was performed on Polygram SIL G/UV 254 pre-coated plastic TLC plates with 0.25 mm silica gel from Macherey-Nagel+Co. Visualization was performed with a 254 nm UV lamp or by using an aqueous solution of $KMnO_4$ (a solution of $KMnO_4$ (1.5 g), $K_2CO_3$ (10 g) and 10% aqueous NaOH (1.25 cm$^3$ in water (200 cm$^3$)).

Silica gel column chromatography was carried out with Flash silica gel (0.040-0.063 mm) from Merck. For the flash chromatography a CombiFlash R$_f$200 system was used.

8,8-dibromobicyclo[5.1.0]octane (26) and (1R,7S,8r)-8-bromobicyclo[5.1.0]octane (27) (see e.g., Seyfert et al., *Orgmet. Chem.* 1975, 88, 255-286), 4,7-dihydro-1,3-dioxepin (17) (see e.g., Brannock et al., *J. Org. Chem.* 1956, 1366-1368), methyl diazoacetate (see e.g., Womack et al., *Org. Synth.* 1955, 3, 392), rhodamine piperazine chloride (see e.g., Nguyen et al., *Org. Lett.* 2003, 5, 3245-3248) and 4-[[4-fluoro-3(4-(N-(2-aminoethyl)-5-oxo-pentanamide)piperazine-1-carbonyl)phenyl]methyl]methyl]-2H-phthalazin-1-one (PARP1 inhibitor) (see e.g., Menear et al., *J. Med. Chem.* 2008, 51, 6581-6591) were prepared using standard literature procedures.

Cell Lines

HT1080 cells from ATCC were grown in DMEM supplemented with 10% fetal bovine serum, 100 I.U. penicillin, 100 µg/mL streptomycin, and 2 mM L-glutamine.

PARP1-mCherry Reporter Construct mCherry Protein tagged to subunit VIII of Poly ADP ribose polymerase 1 (PARP1-mRFP) was utilized to identify PARP target protein. PARP1-mCherry was constructed by PCR of human PARP1 from Open Biosystems clone 5193735 from the NIH_MGC_114 cDNA library, and cloning into pmCherry-N1 (Clontech) between XhoI and XmaI on Multiple Cloning site.

Live Cell Fluorescence Microscopic Imaging

HT1080 cells were plated at 5000 cells per well in 96-well black µ-clear bottom plates (Grenier Bio-One) and were grown for 48-72 hrs. One day before imaging, cells were transiently transfected with PARP1-mCherry DNA construct. 6 µL of Fugene 6 (Promega) was diluted with 92.4 µL of GIBCO Opti-MEM media for 5 minutes at room temperature. After the incubation, 1.6 µL of PARP1-mCherry DNA construct (1.2 µg/µL) was added to the solution. DNA mixture was incubated at room temperature for 15 minutes. Meanwhile, media of the cells were changed with RPMI media containing 10% FBS without antibiotics. After the incubation of DNA and Fugene 6 mixture solution for 15 minutes, 5 µL of the complex was added to the corresponding wells. Cells were incubated at 37° C. 5% $CO_2$ humidified incubator for overnight. Expression of fluorescent protein was briefly checked with florescent microscope. 2 µL of 250 µM TCO drug was added to the corresponding wells. After 30 minutes incubation, media was removed and 50 µM CFDA-Tz (see e.g., Yang et al., *Angew. Chem. Int. Ed.* 2012, 51, 6598-6603) was added to the corresponding wells and the cells were incubated for 30 minutes. After washing with growth media two times for 5 minutes each, cells were incubated for 2 h washing with the media every 30 minutes. Then they were fixed with 4% paraformaldehyde for 10 minutes. After washing with PBST three times for 5 minutes each, cells were imaged with Delta vision fluorescent microscope.

Example 1—Preparation and Characterization of DO-TCO (22)

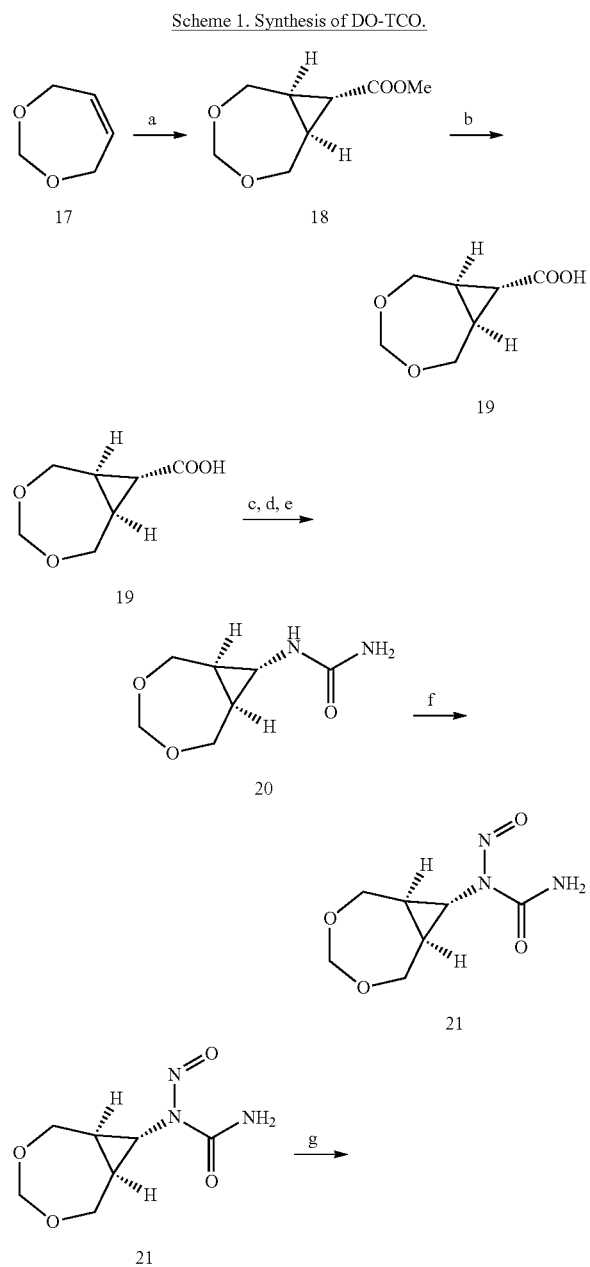

Scheme 1. Synthesis of DO-TCO.

-continued

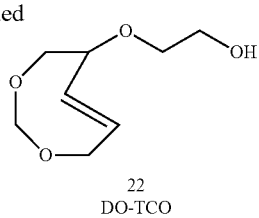

22
DO-TCO a) N$_2$CHCOOMe, 0.24 mol % Rh$_2$(OAc)$_4$, r.t., 44%;
b) LiOH, water, THF, r.t., 93%;
c) Et$_3$N, ethyl chloroformate, acetone, 0° C.;
d) NaN$_3$, water;
e) toluene, 105° C., NH$_3$ in THF, 0° C., 88% for three steps;
f) NaOAc, N$_2$O$_4$, Et$_2$O, 0° C., 72%;
g) NaHCO$_3$, ethylene glycol, r.t., 32%.

Preparation of this compound was based on known methods (see, e.g., Jendralla, H. *Chem. Ber.* 1982, 115, 201-209), and started from commercially available dioxepin 17 which was reacted with methyl diaza acetate in the presence of catalytic Rh$_2$(OAc)$_4$ to furnish cyclopropyl carboxylate 18, which was subsequently subjected to hydrolysis using aqueous LiOH. The resulting acid 19 was transformed to the urea 20 in excellent yields using the Curtius rearrangement. Nitrosation using N$_2$O$_4$ in diethyl ether afforded nitrosourea 21 in good yields. In the last step we used ethylene glycol as solvent and nucleophile in the ring opening in order to convert 21 to a new cyclooctene (22, DO-TCO) having an OH handle for further conjugation. This synthesis involves eight steps and four intermediates are isolated.

For example, step g) of Scheme 1 was performed as follows: 1-((1R,7S,8r)-3,5-dioxabicyclo[5.1.0]octan-8-yl)-1-nitrosourea (2.0 g, 10 mmol, 1.0 equiv) and sodium bicarbonate (1.68 g, 20 mmol, 2.0 equiv) were mixed and ethylene glycol (8 mL, 128 mmol, 12.8 equiv) was added. The resulting suspension was stirred until the yellow color disappeared (approximately 4 h), then the crude reaction mixture was added to saturated aqueous NaNO$_3$ (40 mL) and was extracted with THF (4×15 mL). Most of the THF was then removed on a rotary evaporator. To the resulting residue was added saturated aqueous NaNO$_3$ (30 mL) and the mixture was extracted using THF (3×10 mL). The resulting THF solution was extracted with a 16% by weight aqueous AgNO$_3$ solution (30 mL). The aqueous phase was washed with THF (3×10 mL), which was discarded. Solid NaCl was added to give a saturated salt solution. The resulting precipitates were filtered and washed with a small amount of water and THF. The filtrate was then extracted with THF (4×15 mL). The combined THF phases were dried over MgSO$_4$ and the solvent was removed by rotary evaporation. This gave 850 mg of crude product. Purification on a REDISEP® Gold Diol column (50 g) using 100% Et$_2$O as eluent and a flow rate of 20 mL/min afforded (E)-2-((5,8-dihydro-4H-1,3-dioxocin-5-yl)oxy)ethanol (550 mg, 32%) with a purity of 95%.

$^1$H NMR (500 MHz, CDCl$_3$) δ 6.18 (ddd, J=16.9, 10.7, 3.5 Hz, 1H), 5.82 (dd, J=16.7, 9.3 Hz, 1H), 5.20 (d, J=8.1 Hz, 1H), 4.52 (dd, J=9.6, 3.6 Hz, 1H), 4.31 (td, J=9.0, 5.3 Hz, 1H), 4.24 (m, 2H), 4.00 (t, J=10.2 Hz, 1H), 3.80-3.75 (m, 2H), 3.75-3.69 (m, 1H), 3.65-3.59 (m, 1H), 3.22 (dd, J=11.6, 8.9 Hz, 1H); $^{13}$C NMR (126 MHz, D$_2$O) δ 138.52, 135.42, 97.48, 82.55, 75.95, 73.08, 70.88, 60.35; HRMS (ESI) calcd. for C$_8$H$_{15}$O$_4$ [M+H]$^+$: 175.0965, found: 175.0971.

Kinetic studies on the reaction of DO-TCO (22) with benzylamino tetrazine in PBS at 37° C. gave a second order rate constant of k$_2$=(332±3) dm$^3$ mol$^{-1}$ s$^{-1}$), which is two orders of magnitude lower than the corresponding value measured for TCO-OH (see Example 23). This result is surprising, given that DO-TCO (22) is expected to have much larger internal strain than TCO-OH. Without being bound by any particular theory, there are two possible causes of this unexpectedly low cycloaddition reactivity observed for DO-TCO. The first of which is the additional steric constraints introduced by the glycol moiety adjacent to the trans double bond and the second is a reduction of the kinetic rate enhancement typically observed for this type of cycloaddition in highly polar solvents: a significant rate enhancement was observed both for [4+2] and [3+2] type cycloadditions in water as to compared to the rates of the same reactions in non-protic solvents. Literature studies show that this rate acceleration can be several hundred fold when aqueous solutions are used as media in Diels-Alder reactions; one particular example of iEDDA of tetrazines and alkenes also showed over 100 fold enhancement in water.

Example 2—Preparation and Characterization of EG-TCO (28)

Scheme 2. Synthesis of EG-TCO.

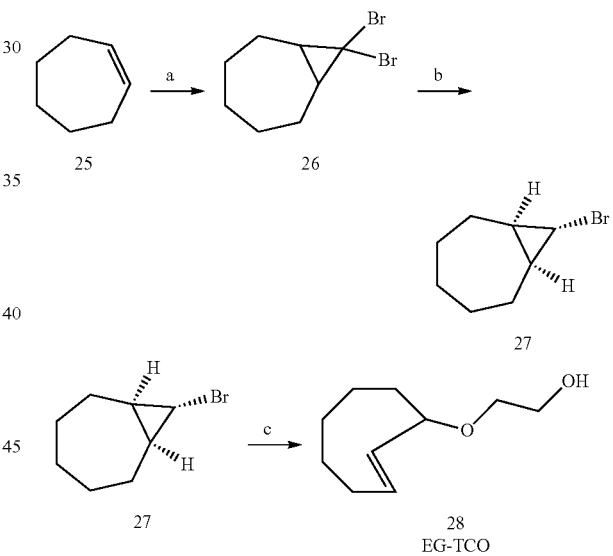

28
EG-TCO a) CHBr$_3$, tBuOK, pentane, 0° C., 80%;
b) BuLi, THF, Et$_2$O, -100° C. then MeOH, -78 → 0° C., 70%;
c) AgClO$_4$, ethylene glycol, r.t., 62%.

For example, step c) of Scheme 2 was performed as follows: To (1R,7S,8r)-8-bromobicyclo[5.1.0]octane (1.01 g, 5.3 mmol, 1.00 equiv) was added ethylene glycol (2 mL). To this solution was added AgClO$_4$ (2.2 g, 10.6 mmol, 2.00 equiv) in ethylene glycol (4 mL). The resulting mixture was stirred for 7 h. After filtration, the remaining solids were washed with DCM. The combined filtrates were added to 10% AgNO$_3$ solution (30 mL). This mixture was then extracted four times with DCM and the DCM extracts were discarded. To the aqueous phase, NaCl was added to obtain a saturated salt solution. The resulting precipitate was filtered and washed with DCM (4×10 mL). The organic and aqueous phases were separated, and the aqueous phase was extracted with DCM (5×15 mL). The combined organic phases were dried with anhydrous MgSO$_4$ and concentrated by rotary evaporation, affording 700 mg (78%) of product with a purity of 90-95%. The sample was purified by flash chromatography on REDISEP® Gold silica gel (24 g, 35 mL/min flow rate) for analytical purposes, employing a gradient of 10 to 15% EtOAc in hexane over 11.5 minutes, to give pure (E)-2-(cyclooct-2-en-1-yloxy)ethanol (550 mg, 79% recovery).

$^1$H NMR (500 MHz, CDCl$_3$) δ 5.72 (ddd, J=15.2, 11.0, 3.7 Hz, 1H), 5.48 (dd, J=16.2, 9.4 Hz, 1H), 3.94 (td, J=9.8, 5.5 Hz, 1H), 3.79-3.70 (m, 2H), 3.70-3.62 (m, 1H), 3.56-3.49 (m, 1H), 2.45-2.37 (m, 1H), 2.22-2.14 (m, 2H), 2.06-1.91 (m, 2H), 1.92-1.73 (m, 2H), 1.56-1.44 (m, 1H), 1.46-1.33 (m, 1H), 0.94-0.84 (m, 1H), 0.81-0.71 (m, 1H); $^{13}$C NMR (126 MHz, CDCl$_3$) δ 134.83, 133.72, 84.47, 70.19, 61.97, 41.52, 35.65, 35.51, 28.98, 27.50; HRMS (ESI) calcd. for C$_{10}$H$_{19}$O$_2$ [M+H]$^+$: 171.1380, found: 171.1388; calcd. for C$_{10}$H$_{21}$NO$_2$ [M+NH$_4$]$^+$: 188.1645, found: 188.1654.

Surprisingly, the second order rate constant for 28 proved to be only k$_2$=(600±6) dm$^3$ mol$^{-1}$ s$^{-1}$ in PBS at 37° C. (see Example 23). While it is still fifty times lower than the second order rate constant for TCO-OH, it is double the value measured for DO-TCO (22). These rate constant data indicate that the low cycloaddition reactivities of EG-TCO and DO-TCO with benzyl amino tetrazine, in comparison to TCO-OH, are to a great degree the result of steric hindrance exerted by the ether group. This alone, however, does not fully explain the observation that DO-TCO has a smaller second order rate constant than EG-TCO. It can be assumed that in the reaction of DO-TCO the hydrophobic interactions cannot play such a prominent role as in the reaction of the EG-TCO, because of the highly increased polarity of the cyclooctene.

Example 3—Preparation of 3PEGMe-TCO (37)

Scheme 3. Synthesis of 3PEGMe-TCO.

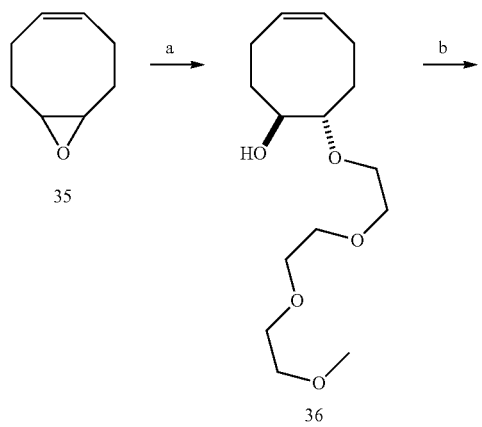

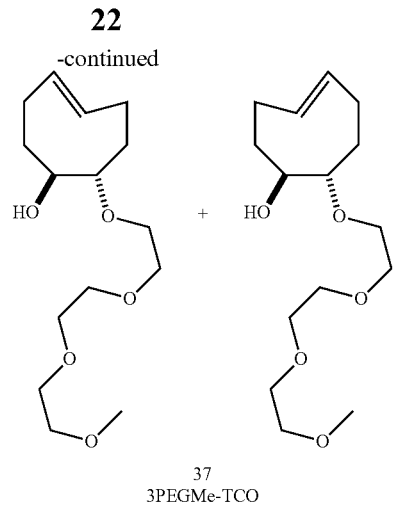

a) 3PEGMe, Er(OTf)$_3$, r.t., 41%; b) hv, methyl benzoate, 4:1 Et$_2$O/hexanes 64%.

The synthesis of 37 begins with ring opening of the epoxide of (Z)-9-oxabicyclo[6.1.0]non-4-ene (35) in the presence of triethylene glycol monomethyl ether (3PEGMe) and erbium triflate to afford 36, which is isolated by vacuum distillation of the crude reaction mixture. Cis-compound 36 is then photochemically converted to an approximately 1:1 mixture of two trans isomers (37) using the same apparatus as previously described (see, e.g., Blackman, M. L. et al., *J. Am. Chem. Soc.* 2008, 130, 13518-13519). The product-AgNO$_3$ complex was eluted from the column with Et$_2$O:DCM:MeOH (3:1:1) mixture. The resulting organics were extracted into an aqueous 10% AgNO$_3$ solution. The combined aqueous phases were washed with DCM and the AgNO$_3$ trans-cyclooctene complex was decomposed by the addition of saturated NaCl or saturated NH$_3$ solution. 37 was isolated as a mixture of two trans isomers in 64% overall yield. The separation of the two isomers was not successful using silica flash chromatography; but the separation of the two isomers was possible through preparation of an NHS-carbamate derivatives (see Example 5).

For example, step b) of Scheme 3 was performed as follows: (Z)-8-(2-(2-(2-methoxyethoxy)ethoxy)ethoxy)cyclooct-4-enol (5.2 g, 18 mmol, 1.0 equiv) and methyl benzoate (2.5 g, 18 mmol, 1.0 equiv) were dissolved in 500 mL of a 4:1 Et$_2$O/hexanes mixture. The solution was subjected to UV irradiation for 20 h in a photochemical reactor according to literature procedures (see e.g., Blackman et al., *J. Am. Chem. Soc.* 2008, 130, 13518-13519). The column used for the continuous separation of the product from the reaction mixture contained 7 g silica on the bottom and 35 g AgNO$_3$ impregnated silica on the top (10% AgNO$_3$ content). After 20 h, the product-AgNO$_3$ complex was eluted from the silica column using 500 mL Et$_2$O containing 20% DCM and 20% MeOH. The resulting organics were extracted using an aqueous 10% AgNO$_3$ solution (3×30 mL). The combined aqueous phases were washed with DCM (5×20 mL), which was discarded. Brine was added to the aqueous phase, the solids were filtered, washed with DCM, and the filtrate was extracted with DCM (5×20 mL). The combined DCM phases were dried over anhydrous MgSO$_4$ and the solvent was removed by rotary evaporation. This gave 3.3 g (64%) of product as a 1:1 mixture of two trans-isomers. Attempts to separate the two isomers on silica were unsuccessful.

$^1$H NMR (500 MHz, CDCl$_3$) δ 5.69 (ddd, J=16.0, 10.8, 3.6 Hz, 1H), 5.53 (ddd, J=16.1, 10.7, 3.8 Hz, 1H), 5.47-5.36

(m, 2H), 4.07 (ddd, J=8.2, 6.3, 1.7 Hz, 1H), 3.74-3.57 (m, 20H), 3.56-3.51 (m, 4H), 3.47 (dddd, J=9.9, 5.4, 3.0, 1.5 Hz, 2H), 3.36 (two overlapping singlets, 6H), 3.20 (ddd, J=10.7, 4.9, 1.5 Hz, 1H), 2.43-1.84 (m, 12H), 1.80-1.59 (m, 4H); $^{13}$C NMR (126 MHz, CDCl$_3$) δ 135.36, 132.89, 132.56, 132.47, 85.15, 80.28, 76.27, 71.82, 71.79, 70.97, 70.74, 70.72, 70.61, 70.58, 70.49, 70.42, 68.72, 58.88, 41.12, 38.44, 36.83, 33.00, 32.88, 32.47, 27.65, 27.50; HRMS (ESI) calcd. for $C_{15}H_{29}O_5$ [M+H]$^+$: 289.2010, found: 289.2015.

Example 4—Preparation of OX-TCO (40)

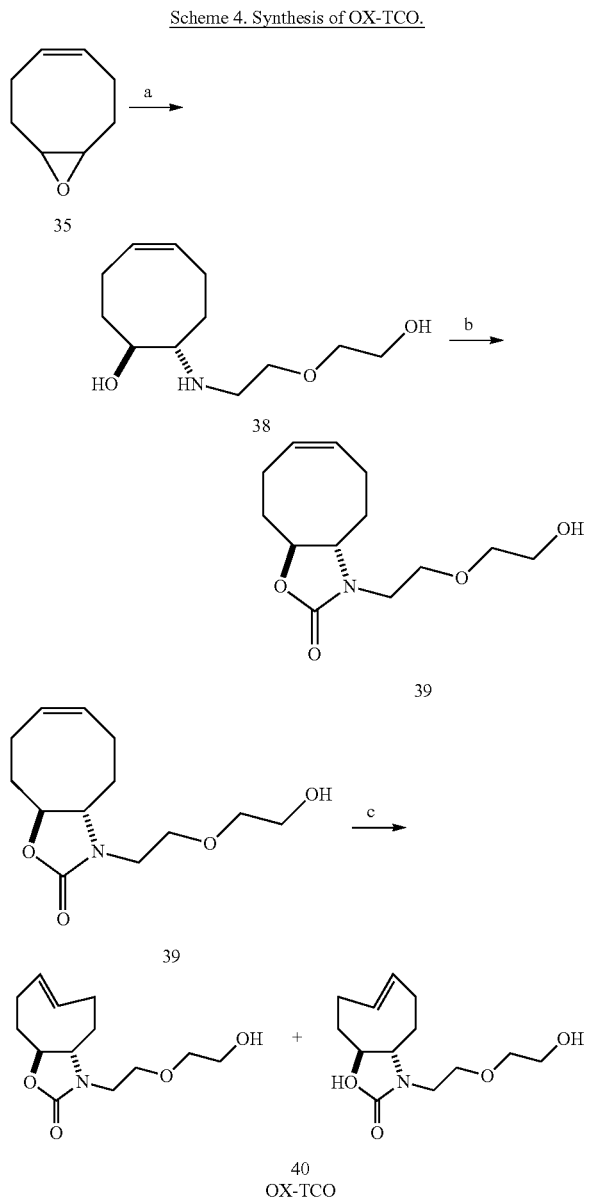

Scheme 4. Synthesis of OX-TCO.

a) 2-(2-aminoethoxy) ethanol, MW, 130° C., 85%;
b) N,N'-disuccinimidyl carbonate, Et$_3$N, acetonitrile, r.t., 92%;
c) hv, methyl benzoate, 1 vol % MeOH in Et$_2$O, 82%.

For the synthesis of compounds 40 (OX-TCO), the reaction was started using (Z)-9-oxabicyclo[6.1.0]non-4-ene (35), and reacting it first with 2-(2-aminoethoxy) ethanol, in a microwave reactor, at 130° C. constant temperature mode. This provided 38 which was then reacted with N,N-disuccinimidyl carbonate overnight yielding compound 39 in excellent yields. 39 was subjected to a photochemical reaction following the same procedure as for compound 36. In this case, diethyl ether containing 1% MeOH was necessary to ensure continuous elution of the unreacted starting material from the AgNO$_3$ impregnated silica. For a good conversion of 39 to the trans-isomers 40, a reaction time 72 hours was required, and the reaction flask was cleaned several times because of the silver plating observed on the inner surface of the glass.

For example, step c) of Scheme 4 was performed as follows: (Z)-3-(2-(2-hydroxyethoxy)ethyl)-3,3a,4,5,9,9a-hexahydrocyclooctal[d]oxazol-2-(8H)-one (3.8 g, 14.8 mmol, 1.0 equiv) and methyl benzoate (2.0 g, 14.8 mmol, 1.0 equiv) were dissolved in Et$_2$O (470 mL) containing 1% MeOH. The solution was subjected to UV irradiation for 80 h in a photochemical reactor according to literature procedures. The column used for the continuous separation of the product from the reaction mixture contained 7 g silica on the bottom and 35 g AgNO$_3$ impregnated silica on the top (10% AgNO$_3$ content). During the course of the reaction the quartz reaction flask was changed twice (at 30 h and 60 h) due to silver plating in the reaction vessel.

After 80 h, the column was washed using 500 mL Et$_2$O containing 5% MeOH and this solution was discarded. The column was then washed with MeOH (500 mL) to elute the product-AgNO$_3$ complex. The MeOH was removed by rotary evaporation at 30° C. and 30 mL of 10% aqueous AgNO$_3$ was added. This solution was washed with DCM (8×10 mL), which was discarded. Brine was added to the remaining aqueous solution, the solids were removed by filtration, washed with DCM, and the filtrate was extracted with DCM several times. The combined DCM phases were dried over anhydrous MgSO$_4$ and the solvent was removed by rotary evaporation. This gave 3.1 g (82%) of product as a 4:1 mixture of two trans-isomers.

$^1$H NMR (500 MHz, CDCl$_3$) δ 5.86 (apparent t, J=4.3 Hz, 2H), 5.59-5.41 (m, 8H), 4.22 (apparent t, J=9.3 Hz, 1H), 4.16-4.06 (m, 4H), 3.74-3.69 (m, 10H), 3.66-3.51 (m, 26H), 3.28-3.19 (m, 5H), 2.59-2.47 (m, 2H), 2.47-2.27 (m, 18H), 2.27-2.13 (m, 12H), 2.13-2.02 (m, 2H), 1.91 (apparent qd, J=12.0, 5.4 Hz, 4H), 1.84-1.72 (m, 1H), 1.63-1.48 (m, 5H); $^{13}$C NMR (126 MHz, CDCl$_3$) δ 157.82, 157.13, 135.96, 135.78, 134.22, 132.61, 83.63, 83.50, 72.31, 72.27, 68.46, 68.44, 64.93, 64.77, 61.65, 53.37, 41.89, 41.68, 40.27, 38.36, 37.41, 34.58, 31.93, 31.79, 25.20, 24.97; calcd. for $C_{13}H_{21}NNaa_4$ [M+Na]$^+$: 278.1363, found: 278.1375.

Example 5—Preparation and Characterization of NHS Carbamates

Scheme 5. Preparation of NHS carbamates from TCOs.

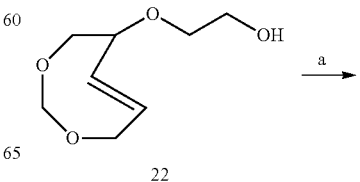

22

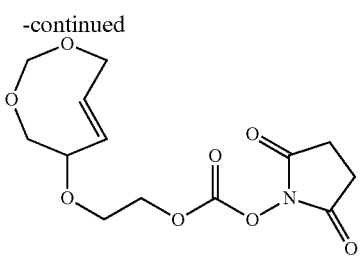

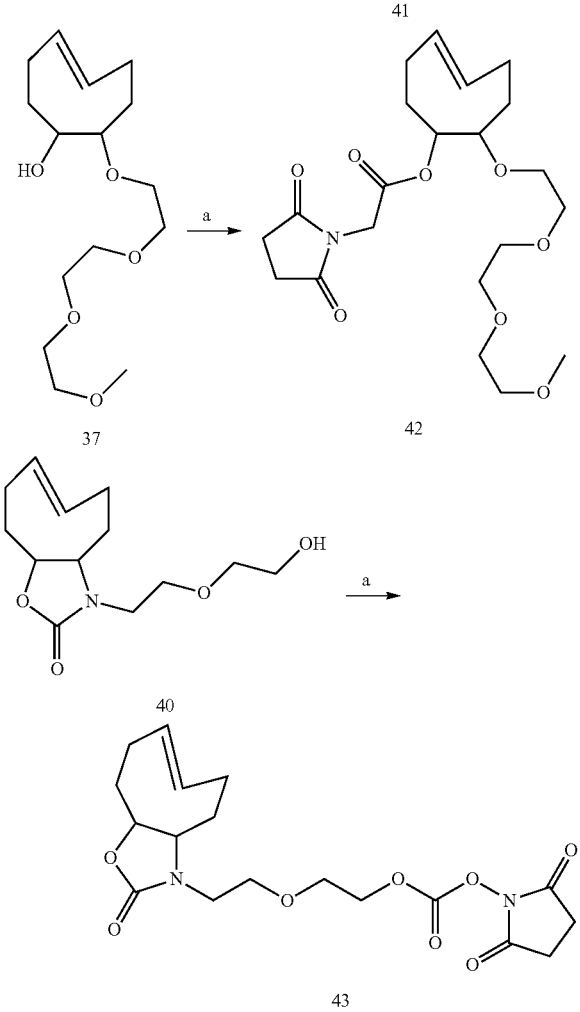

a) MeCN, Et₃N, N,N'-disuccinimidyl carbonate, r.t., 83% for 41, 37% for 42, 71% for 43.

NHS carbamates were prepared from DO-TCO, 3PEGMe-TCO and OX-TCO, using N,N'-disuccinimidyl carbonate as a reagent in the presence of Et₃N in acetonitrile at room temperature (see Examples 17-19). In the case of 37 and 40, an isomeric mixture of the trans compounds was used for the conversion to the NHS carbamate (for simplicity we do not show stereochemistry in Scheme 5). Kinetic measurements for both isomers of 37 were preformed as the two isomers were able to be separated as their N-hydroxysuccinimidyl ester conjugates. However, in the case of 40, it was necessary to measure its kinetics on the 4:1 mixture of isomers as separation attempts were unsuccessful.

For 37 the two rate constants are $k_2=(20643\pm387)$ dm³ mol⁻¹ s⁻¹ and $k_2=(108041\pm2418)$ dm³ mol⁻¹ s⁻¹ in PBS at 37° C. for the reaction with benzylamino tetrazine (see Example 23). This difference in rate constants for the two isomers of 37 may seem unexpected, however, it has been shown that there can be up to one order of magnitude difference in the reactivities of different isomers of TCOs in reactions with tetrazines depending on the position (axial or equatorial) of the substituent opposite to the trans double bond (see, e.g., Rossin, R. et al., *Bioconjugate Chem.* 2013, 24, 1210-1217). The pseudo first order kinetic data for the isomer mixture of 40 fitted well to a single exponential decay at all cyclooctene concentrations used and gave a weighted average second order rate constant of $k_2=(29242\pm636)$ dm³ mol⁻¹ s⁻¹ under the same conditions as was used for compound 37 (see Example 23). This aligns well with the reactivity of TCO-OH.

Example 6—Hydrophilicity and Storage Stability

Bulk samples of the compounds described above in Examples 1-3 were stored at −20° C. for six months. The compounds were found to be stable under these conditions with no indication of degradation or isomerization by ¹H NMR. When (E)-2-((5,8-dihydro-4H-1,3-dioxocin-5-yl)oxy)ethanol (22, DO-TCO) was stored in D₂O, slow isomerization to the cis isomer was observed as confirmed by ¹H NMR. The spontaneous isomerization took almost 5 days at 37° C. and more than 12 days at room temperature. For comparison, the known and highly reactive s-TCO showed at least 5% isomerization after 14 hours in D₂O:DMSO-d₆ δ 10:1 at room temperature. With 22, a similar degree of isomerization was observed only after 63 hours at room temperature in D₂O. In contrast to the slow isomerization observed for DO-TCO, parallel experiments with 3PEGMe-TCO and OX-TCO indicated no isomerization or degradation, a result that is identical to that of TCO-OH.

The chemical stability of the compounds of Examples 1-3 was also investigated in the presence of thiols (cysteine and mercaptoethanol) by NMR in D₂O:DMSO-d₆ 10:1 v/v at 37° C. TCO-OH, EG-TCO, OX-TCO did not show any change after 16 hours. 3PEGMe-TCO did not show any degradation in the presence of cysteine, however, it isomerized to the cis isomer in the presence of mercaptoethanol. s-TCO and DO-TCO both showed isomerization of the trans isomer to the cis isomer in the presence of both thiols as the main reaction together with unidentified side reactions as the emergence of complex patterns in the aliphatic region suggests.

The solutions were prepared by the dilution of a stock solution prepared in DMSO-d₆. An end concentration of 20 mM of the cyclooctenes was used except for the s-TCO, which was used in 10 mM end concentration due to poorer solubility. A 20 mM solution could not be prepared by dilution with D₂O from DMSO-d₆ stock solution without the precipitation of s-TCO. Nucleophiles mercaptoethanol and cysteine were used in 48 mM end concentration. Cysteine precipitated very soon from the solution. In all cases reactions were followed by ¹H NMR.

TCO isomerized very fast in the presence of mercaptoethanol, so a control experiment was performed in which s-TCO was kept in D₂O:DMSO-d₆ (10:1 v/v) at room temperature. Measurements were taken in the following intervals: mercaptoethanol: 0 h, 2 h, 11 h, 17 h and 25 h; cysteine: 0 h, 6 h and 14 h; s-TCO without nucleophile at room temperature: 1 h, 7 h and 14 h.

TCO-OH, EG-TCO, OX-TCO did not show any change under the aforementioned conditions. 3PEGMe-TCO did not show any degradation in the presence of cysteine, however, it isomerized to the cis-isomer in the presence of mercaptoethanol, as shown in Table 1. s-TCO and DO-TCO both showed isomerization of the trans-isomer to the cis-isomer in the presence of cysteine as the main reaction, as shown in Tables 4 and 6. In the presence of mercaptoethanol, isomerization of DO-TCO and s-TCO occurred together with unidentified side reactions as the emergence of complex patterns in the aliphatic region suggests. These observations are summarized in Tables 2-3. In each case the ratio of the integrals of the cis-double bond to the sum of the integrals of the cis- and trans-double bonds was calculate.

TABLE 1

Isomerization of 3PEGMe-TCO in the presence of mercaptoethanol at 37° C.

| t (h) | $I_{cis}$ | $I_{trans}$ | $I_{trans}/(I_{cis} + I_{trans})$ |
|---|---|---|---|
| 0 | 0.17 | 2 | 0.922 |
| 2 | 0.48 | 2 | 0.807 |
| 11 | 0.66 | 2 | 0.752 |
| 17 | 0.69 | 2 | 0.744 |
| 25 | 0.74 | 2 | 0.730 |

TABLE 2

Isomerization of DO-TCO in the presence of mercaptoethanol at 37° C.

| t (h) | $I_{cis}$ | $I_{trans}$ | $I_{trans}/(I_{cis} + I_{trans})$ |
|---|---|---|---|
| 0 | 0 | 2 | 1 |
| 2 | 0.18 | 2 | 0.917 |
| 11 | 0.38 | 2 | 0.840 |
| 17 | 0.42 | 2 | 0.826 |
| 25 | 0.79 | 2 | 0.717 |

TABLE 3

Isomerization of s-TCO in the presence of mercaptoethanol at 37° C.

| t (h) | $I_{cis}$ | $I_{trans}$ | $I_{trans}/(I_{cis} + I_{trans})$ |
|---|---|---|---|
| 0 | 1.19 | 2 | 0.627 |
| 2 | 87 | 2 | 0.023 |
| 11 | 2 | 0 | 0 |
| 17 | 2 | 0 | 0 |
| 25 | 2 | 0 | 0 |

TABLE 4

Isomerization of DO-TCO in the presence of cysteine at 37° C.

| t (h) | $I_{cis}$ | $I_{trans}$ | $I_{trans}/(I_{cis} + I_{trans})$ |
|---|---|---|---|
| 0 | 0 | 2 | 1 |
| 6 | 2 | 0 | 0 |
| 14 | 2 | 0 | 0 |

TABLE 5

Isomerization of s-TCO in the presence of cysteine at 37° C.

| t (h) | $I_{cis}$ | $I_{trans}$ | $I_{trans}/(I_{cis} + I_{trans})$ |
|---|---|---|---|
| 0 | 0.19 | 2 | 0.913 |
| 6 | 1.07 | 2 | 0.652 |
| 14 | 8.42 | 2 | 0.192 |

TABLE 6

Isomerization of s-TCO in $D_2O$:DMSO-$d_6$ (10:1 v/v) at room temperature.

| t (h) | $I_{cis}$ | $I_{trans}$ | $I_{trans}/(I_{cis} + I_{trans})$ |
|---|---|---|---|
| 0 | 0 | 2 | 1 |
| 1 | 0.03 | 2 | 0.985 |
| 7 | 0.06 | 2 | 0.971 |
| 14 | 0.1 | 2 | 0.952 |

From these data it was concluded that while TCO-OH, EG-TCO, OX-TCO and 3PEGMe-TCO are relatively stable in the presence of thiol nucleophiles, DO-TCO and s-TCO undergo isomerization/decomposition. In the presence of mercaptoethanol most of the s-TCO disappeared within the first two hours of the experiment, while DO-TCO was almost unaffected within the same period. In the presence of cysteine the isomerization of DO-TCO proved to be much faster than that of s-TCO. While for the DO-TCO no trans-compound was present after 6 hours, the s-TCO still contained 65% trans-isomer.

Example 7—Imaging and Bioconjugation

The utility of the compounds of Examples 1-3 was investigated using a previously validated model system employing modified AZD2281-TCO conjugates to target PARP1. It has been shown that the 4-NH-piperazine of AZD2281 tolerates a diverse range of capping groups without significantly decreasing PARP1 binding affinity. A previous study reported AZD2281-TCO, which is a modification of AZD2281 using the NH-piperazine anchor point. AZD2281-TCO was then used in live-cell imaging with fluorophore-tetrazine derivatives (see. e.g., Blackman, M. L. et al., J. Am. Chem. Soc. 2008, 130, 13518-13519). Similarly, compounds AZD2281-DO-TCO, AZD2281-3PEGMe-TCO and AZD2281-OX-TCO were prepared and used to evaluate their performance in in vivo imaging experiments (see Examples 20-22).

Scheme 6. Preparation of AZD2281 conjugates.

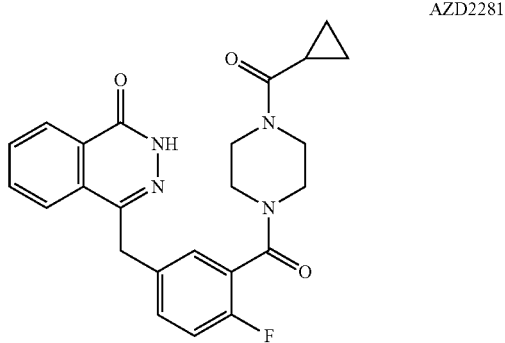

AZD2281

29
-continued
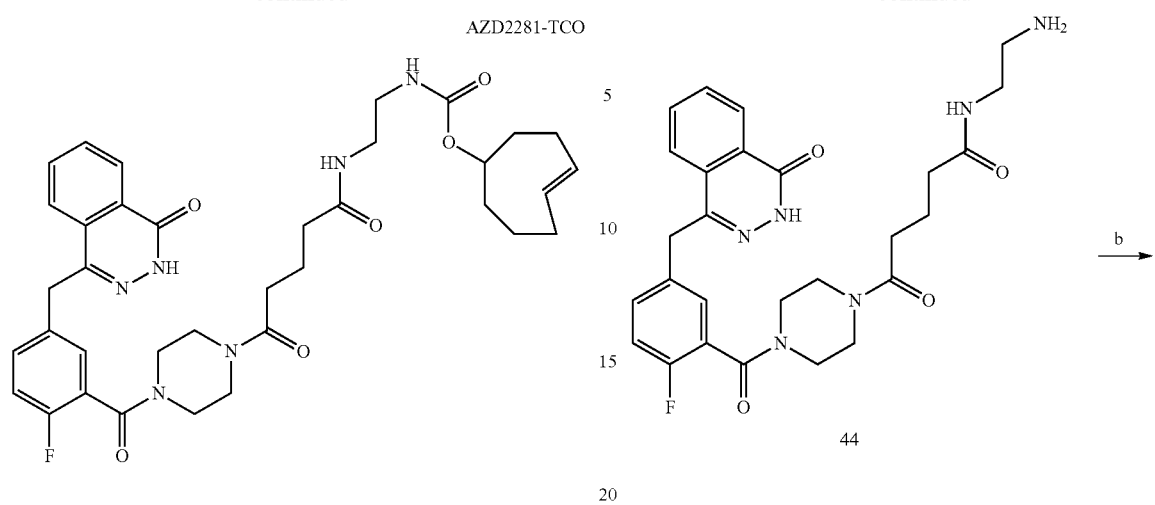
30
-continued
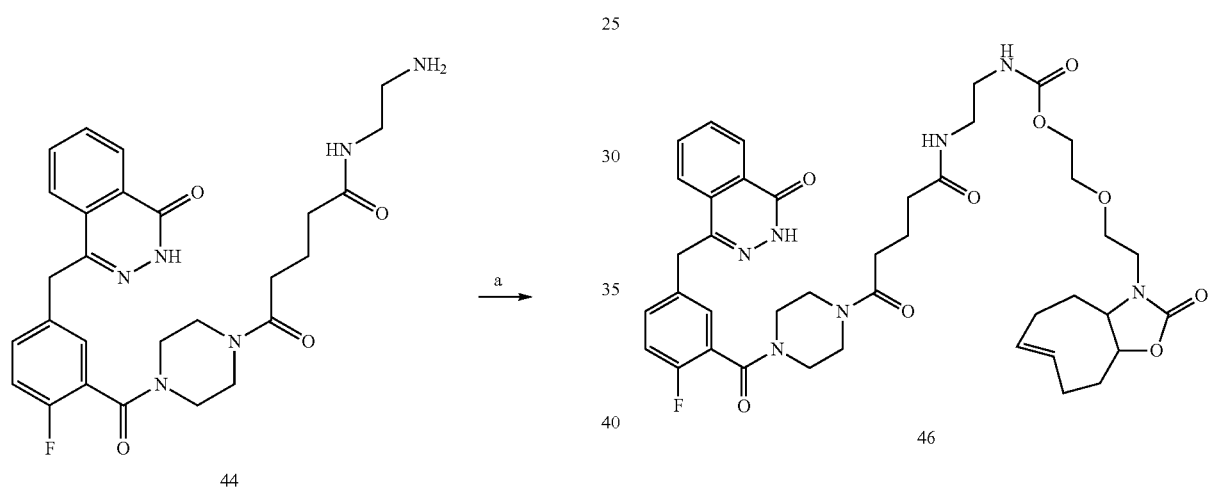
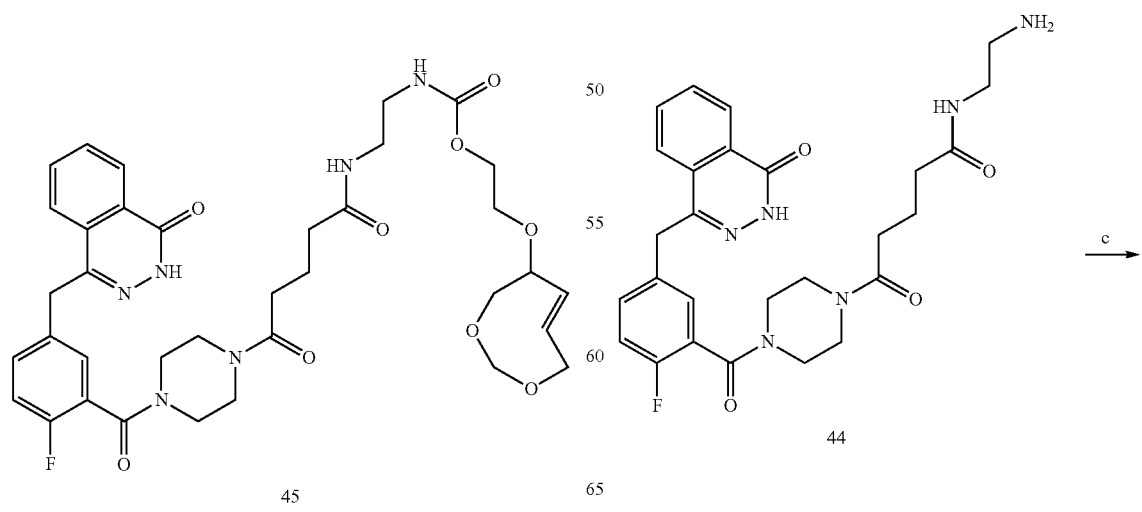

-continued

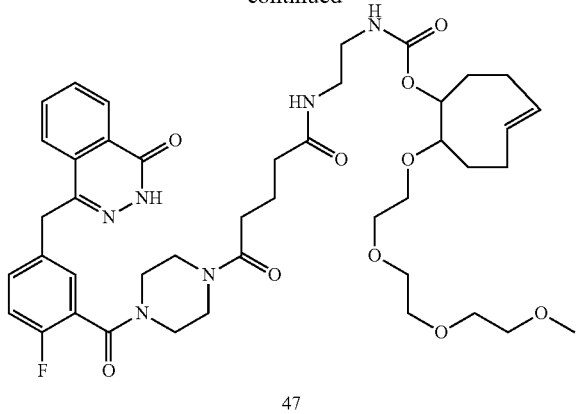

47 a) DMF, Et₃N, then 41 in DCM, r.t., 54%; b) DMF, Et₃N, then 42 in DCM, r.t., 70%;
c) DMF, Et₃N, then 43 in DCM, r.t., 74%.

The conjugates were tested in imaging experiments (FIG. 1). An advantage of the new trans cyclooctene derivatives lies in their improved solubility in DMSO/water mixtures. Bioorthogonal imaging experiments of PARP protein in HT1080 cells (expressing PARP1 fused to mCherry) were successful with all three new compounds, (FIG. 1). The imaging experiments were performed by treating HT1080 cells (expressing PARP1 fused to mCherry) with 5 μM compound 45 (a-d), 46 (e-h) and 47 (i-l) for 30 minutes. After washing with growth media three times for 5 minutes each, cells were incubated for 30 minutes with 1 μM of CFDA-Tz for bio-orthogonal reaction inside the live cells. Following fixation, 40× images were collected by deconvolution microscopy a, e, i) bright field images; b, f, j) Olaparib-TCO/Tz-CFDA staining; c, g, k) PARP1-mCherry, d, h, l) merged images (see FIG. 1). Scale bar: 10 μm.

Example 8—Preparation of (1R,7S,8r)-methyl 3,5-dioxabicyclo[5.1.0]octane-8-carboxylate (18)

Rhodium acetate (250 mg, 0.57 111 mol, 2.4×10⁻³ equiv) was dissolved in 4,7-dihydro-1,3-dioxepine (240 g). To this was added a solution of methyl diazoacetate (240 g, 2.4 mol, 1.0 equiv) in 4,7-dihydro-1,3-dioxepine (350 g) at the rate of 1 drop per second (approximately 4 h total). The total amount of 4,7-dihydro-1,3-dioxepine used was approximately 2.5 equivalents with respect to methyl diazoacetate. After stirring the reaction overnight, excess 4,7-dihydro-1,3-dioxepine was removed by vacuum distillation. To the remaining residue, Et₂O and petroleum ether were added (1:1 mixture, 150 mL). After storing overnight at −20° C. the resulting crystals were filtered, giving pure (1R,7S,8r)-methyl 3,5-dioxabicyclo[5.1.0]octane-8-carboxylate (47 g, 11.4%). A second batch of product was obtained from the filtrate by removal of the solvent and subsequent distillation. Additional (1R,7S,8r)-methyl 3,5-dioxabicyclo[5.1.0]octane-8-carboxylate was obtained by collecting fractions distilling between 90° C. and 120° C. at 3 to 6 mBar. This gave semi pure (1R,7S,8r)-methyl 3,5-dioxabicyclo[5.1.0]octane-8-carboxylate (150 g, 36%) containing less than 10% impurities. Both the pure and semi-pure product were suitable for subsequent reactions.

¹H NMR (500 MHz, CDCl₃) δ 4.92 (d, J=7.2 Hz, 1H), 4.20 (d, J=7.2, Hz, 1H), 4.14 (dt, J=13.1, 2.0 Hz, 2H), 3.99-3.94 (m, 2H), 3.68 (s, 3H), 2.13 (t, J=4.9 Hz, 1H), 1.80-1.77 (m, 2H); ¹³C NMR (101 MHz, CDCl₃) δ 174.11, 99.76, 68.52, 51.76, 27.46, 18.87; HRMS (ESI) calcd. for C₈H₁₃O₄ [M+H]⁺: 173.0808, found: 173.0809.

Example 9—Preparation of (1R,7S,8r)-3,5-clioxabicyclo[5.1.0]octane-8-carboxylic acid (19)

(1R,7S,8r)-methyl 3,5-dioxabicyclo[5.1.0]octane-8-carboxylate (43 g, 0.25 mol, 1.00 equiv) was dissolved in THF (30 mL). To this solution water (30 mL) was added and the mixture was cooled in an ice bath. To this was slowly added LiOH (12 g, 0.50 mol, 2.00 equiv) in water (120 mL). The resulting mixture was stirred for 2.5 h at room temperature. After stirring for 2.5 h at room temperature, the reaction was quenched by addition of 5 N HCl (80 mL, prepared from a 10 N HCl stock solution and ice). The mixture was extracted with DCM (5×50 mL) and the solvents were removed by rotary evaporation. Trituration of the resulting residue with petroleum ether afforded pure (1R,7S,8r)-3,5-dioxabicyclo[5.1.0]octane-8-carboxylic acid (36.9 g, 93%) as a white crystalline solid.

¹H NMR (500 MHz, CDCl₃) δ 4.93 (dd, J=7.1, 1.8 Hz, 1H), 4.25-4.09 (m, 3H), 3.97 (d, J=13.0 Hz, 2H), 2.12 (t, J=4.8 Hz, 1H), 1.84 (dd, J=5.1, 2.7 Hz, 2H); ¹³C NMR (126 MHz, CDCl₃) δ 179.87, 99.72, 68.35, 28.20, 18.82.

Example 10—Preparation of 1-((1R,7S,8r)-3,5-dioxabicyclo[5.1.0]octan-8-yl)urea (20)

To a solution of (1R,7S,8r)-3,5-dioxabicyclo[5.1.0]octane-8-carboxylic acid (2.70 g, 17.1 mmol, 1.0 equiv) in acetone (12 mL), Et₃N (1.99 g, 19.6 mmol, 1.15 equiv) in acetone (24 mL) was added dropwise at 0° C. Ethyl chloroformate (2.32 g, 21.3 mmol, 1.25 equiv) in acetone (6 mL) was added to the resulting solution at 0° C. The ethyl chloroformate addition resulted in the formation of a white precipitate. This suspension was stirred at 0° C. for 30 min and then sodium azide (1.71 g, 26.3 mmol, 1.54 equiv) in water (3 mL) was added. Upon the addition of the sodium azide, a light pink color developed. The resulting suspension was maintained at 0° C. for 1 h with stirring and then was poured onto ice. The resulting homogenous mixture was extracted with toluene (10×20 mL). The organic phase was dried over MgSO₄ for 16 h, concentrated to 50 mL on a rotary evaporator and heated to 100-105° C. until the gas evolution ceased. The yellow solution was cooled to 0° C. and ammonia (68.2 mL of 0.5 M solution in THF, 34.1 mmol, 2.00 equiv) was added slowly. The resulting white suspension was stirred for 1 h at room temperature. After stirring, the THF was removed by rotary evaporation. The suspension was cooled to 0° C., the white precipitate was filtered and then washed with a few mL of Et₂O and petroleum ether and dried, yielding 1-((1R,7S,8r)-3,5-dioxabicyclo[5.1.0]octan-8-yl)urea (2.58 g, 88%) as a white solid.

¹H NMR (500 MHz, DMSO-d₆) δ 6.11 (d, J=3.9 Hz, 1H), 5.42 (s, 2H), 4.70-4.39 (m, 2H), 4.22-3.96 (m, 2H), 3.72 (d, J=12.1, 2H), 2.75 (dd, J=3.7, 3.7 Hz, 1H), 1.45-1.08 (m, 2H). ¹³C NMR (126 MHz, DMSO-d₆) δ 158.97, 99.76, 70.32, 33.11, 26.17.

Example 11—Preparation of 1-((1R,7S,8r)-3,5-dioxabicyclo[5.1.0]octan-8-yl)-1-nitrosourea (21)

To a suspension of 1-((1R,7S,8r)-3,5-dioxabicyclo[5.1.0]octan-8-yl)urea (55.0 g, 319.4 mmol, 1.00 equiv) and sodium acetate (52.0 g, 638.9 mmol, 2.00 equiv) in Et₂O (600 mL) was added liquid N₂O₄ (39 g, 425 mmol, 1.33 equiv) dissolved in Et$_2$O (500 mL) at −45° C. The mixture was subsequently stirred at 0-10° C. for 1.5 h. After stirring, the solids were filtered off, washed with cold Et$_2$O (3×30 mL) kept to be worked up later. The solid residue was extracted with DCM until only white precipitate remained on the filter (approximately 20×50 mL DCM). The combined DCM extracts were concentrated by rotary evaporation, 50 mL hexane was added, and the resulting yellow precipitate was filtered giving 1-((1R,7S,8r)-3,5-dioxabicyclo[5.1.0]octan-8-yl)-1-nitrosourea (38 g, 59%). A second batch of product was obtained from the remaining Et$_2$O reaction solution. The Et$_2$O reaction solution was washed several times with cold saturated NaHCO$_3$ and concentrated to 40 mL by rotary evaporation. To this concentrate was added hexanes (20 mL). Filtration of the precipitate gave an additional 8 g (13%) of 1-(0R,7S,8r)-3,5-dioxabicyclo[5.1.0]octan-8-yl)-1-nitrosourea with a combined yield of 46 g (72%).

$^1$H NMR (250 MHz, DMSO-d$_6$) δ 7.98 (s, 1H), 7.84-7.56 (m, 1H), 4.80 (d, J=7.4 Hz, 1H), 4.27-4.06 (m, 3H), 3.93 (d, J=12.8 Hz, 2H), 2.57 (t, J=4.5 Hz, 1H), 1.37 (t, J=3.3 Hz, 2H); $^{13}$C NMR (63 MHz, DMSO-d$_6$) δ 154.00, 99.05, 68.23, 27.64, 26.18.

Example 12—Preparation of 8,8-dibromo-3,5-dioxabicyclo[5.1.0]octane (23)

In an adaption of literature procedures (see e.g., Fedorenko et al., *Mendeleev Commun.* 2007, 17, 170-171), bromoform (28.6 g, 112 mmol, 1.50 equiv), cetrimonium bromide (2.25 g, 6.1 mmol, 0.08 equiv), Et$_3$N (2 drops) and DCM (20 mL) were mixed and stirred for 20 min. To this solution was added 4,7-dihydro-1,3-dioxepine (7.53 g, 75.3 mmol, 1.00 equiv) and stirring was continued for an additional 10 min. The mixture was cooled in a NaCl/ice bath and 60 g of a 50% aqueous NaOH solution was added dropwise. After stirring the resulting brown suspension for 40 h at room temperature, 30 mL water, 30 mL DCM, and 3 g activated charcoal were added. Following filtration of the mixture, the two phases of the filtrate were separated and then the aqueous phase was extracted using DCM (3×20 mL). The combined DCM phases were dried over MgSO$_4$, the solvent was removed by rotary evaporation, and the crude product was purified by flash chromatography on silica gel (80 g, 60 mL/min flow rate) using 5% EtOAc in hexane as eluent. Fractions containing the product were combined and the solvent was removed, giving a yellow oil which partially solidified. Trituation with 10 mL pentane at 0° C. gave pure 8,8-dibromo-3,5-dioxabicyclo[5.1.0]octane (12.6 g, 62%) as white crystals. The product can be visualized on TLC in UV if concentrated (R$_f$=0.21 using 5% EtOAc in hexane).

$^1$H NMR (250 MHz, CDCl$_3$) δ 5.05 (d, J=7.1 Hz, 1H), 4.68-4.53 (m, 2H), 4.49 (d, J=7.1 Hz, 1H), 3.63 (dd, J=13.2, 6.5 Hz, 2H), 2.23 (dd, J=8.5, 4.5 Hz, 2H); $^{13}$C NMR (63 MHz, CDCl$_3$) δ 101.37, 71.83, 35.35, 34.70.

Example 13—Preparation of (1R,7S,8s)-8-bromo-3,5-dioxabicyclo[5.1.0]octane (24)

In an adaptation of the literature procedures, 8,8-dibromo-3,5-dioxabicyclo[5.1.0]octane (5.44 g, 20 mmol, 1.00 equiv) was dissolved in anhydrous Et$_2$O (80 mL) under nitrogen. The solution was cooled to −78° C. in a dry ice/acetone bath and n-BuLi (14 mL, 1.6 M in hexane, 22.4 mmol, 1.12 equiv) was added slowly via cannula alongside the inner wall of the flask. During the addition a white precipitate formed. The heterogeneous mixture was kept at −78° C. for 80 min, then 3 mL of methanol was added and stirring was continued for an additional 40 min at −78° C. Water (0.5 mL) was then added to quench the reaction and the mixture was warmed to room temperature. The mixture was dried by addition of MgSO$_4$ and then filtered. The solvents were evaporated and the crude product was dissolved in pentane and filtered again. The pentane was then removed by rotary evaporation. The resulting light yellow oil was triturated with 5 mL pentane at −10° C. giving pure (1R,7S,8s)-8-bromo-3,5-dioxabicyclo[5.1.0]octane (2.44 g, 63%) as white crystals.

$^1$H NMR (500 MHz, CDCl$_3$) δ 4.88 (d, J=7.2 Hz, 1H), 4.21 (dt, J=13.0, 2.0 Hz, 2H), 4.17 (d, J=7.3 Hz, 1H), 4.00-3.81 (m, 2H), 3.24 (tt, J=4.1, 0.6 Hz, 1H), 1.65-1.62 (m, 2H); $^{13}$C NMR (63 MHz, CDCl$_3$) δ 99.75, 68.44, 28.43, 18.25.

Example 14—Preparation of (Z)-8-(2-(2-(2-methoxyethoxy)ethoxy)ethoxy)cyclooct-4-enol (36)

(Z)-8-(2-(2-(2-methoxyethoxy)ethoxy)ethoxy)cyclooct-4-enol was prepared via a procedure analogous to literature methods (see e.g., Dalpozzo et al., *Synthesis*, 2009, 20, 3433-3438). Epoxide 9-oxabicyclo[6.1.0]nonane (10.8 g, 86 mmol, 1.0 equiv), tri(ethylene glycol)monomethyl ether (17.0 g, 103 mmol, 1.2 equiv) and erbium triflate (5.3 g, 8.6 mmol, 0.1 equiv) were mixed in this order and stirred overnight in a closed flask. The reaction was quenched with the addition of saturated NaHCO$_3$. The precipitate was filtered and washed several times with DCM. The aqueous filtrate was extracted with DCM, the combined DCM phases were dried over anhydrous MgSO$_4$, and the solvents were removed via rotary evaporation. Short path distillation gave 4 g of tri(ethylene glycol)monomethyl ether (at 0.1 torr, 40-60° C. bath temperature) and (Z)-8-(2-(2-(2-methoxyethoxy)ethoxy)ethoxy)cyclooct-4-enol (10.3 g, 41%), which distilled at 0.1 torr, and a bath temperature of 140-160° C. The distilled (Z)-8-(2-(2-(2-methoxyethoxy) ethoxy)ethoxy) cyclooct-4-enol contained 5% tri(ethylene glycol) monomethyl ether and was used in subsequent reactions without further purification.

$^1$H NMR (500 MHz, CDCl$_3$) δ 5.68-5.40 (m, 2H), 3.78-3.72 (m, 1H), 3.72-3.63 (m, 1H) 3.63-3.56 (m, 8H), 3.56-3.46 (m, 3H), 3.35-3.29 (m, 4H), 2.52-2.22 (m, 2H), 2.21-1.93 (m, 4H), 1.73-1.44 (m, 2H); $^{13}$C NMR (126 MHz, CDCl$_3$) δ 129.58, 128.10, 83.08, 72.97, 71.75, 70.44, 70.41, 70.37 (two overlapping signals), 69.28, 58.85, 32.07, 29.59, 23.20, 22.67; calcd. for C$_{15}$H$_{29}$O$_5$ [M+H]$^+$: 289.2010, found: 289.2020.

Example 15—Preparation of (Z)-8-((2-(2-hydroxyethoxy)ethyl)amino)cyclooct-4-enol (38)

To 9-oxabicyclo[6.1.0]nonane (3.0 g, 24 mmol, 1.0 equiv) was added 2-(2-aminoethoxy)ethanol (4.8 g, 48 mmol, 2.0 equiv) and the resulting mixture was heated in a microwave reactor for 1 h at 130° C. in constant temperature mode. After 1 h, the reaction was not complete, so heating was continued for an additional 1 h at 150° C. Trituration of the cooled reaction mixture with Et$_2$O afforded 2.0 g of white crystals.

An additional batch of (Z)-8-((2-(2-hydroxyethoxy)ethyl)amino)cyclooct-4-enol was obtained from the reaction filtrate. First, the filtrate was concentrated in vacuo, dissolved in excess 1N HCl, and washed with DCM (5×30 mL). The organic phase was discarded. The aqueous phase was basified by addition of 6N NaOH and extracted with DCM (8×30 mL). The combined DCM phases were dried over anhydrous MgSO$_4$, the solvent was removed by rotary evaporation and the residue was seeded with crystals from the initial batch of product. Trituration with Et$_2$O afforded an additional 2.6 g of white crystals. The overall yield of (Z)-8-((2-(2-hydroxyethoxy)ethyl)amino)cycloct-4-enol was 4.6 g (85%).

$^1$H NMR (500 MHz, CDCl$_3$) δ 5.62 (dt, J=10.8, 7.1 Hz, 1H), 5.49 (dddd, J=10.6, 8.3, 7.0, 1.2 Hz, 1H), 3.65 (td, J=4.5, 0.9 Hz, 2H), 3.57-3.44 (m, 4H), 3.32 (dddd, J=8.7, 7.7, 3.5, 0.9 Hz, 1H), 2.94 (dddd, J=12.7, 7.4, 4.3, 1.0 Hz, 1H), 2.62 (dddd, J=12.9, 4.8, 3.7, 1.0 Hz, 1H), 2.50-2.40 (m, 1H), 2.37-2.28 (m, 1H), 2.22-2.05 (m, 3H), 2.01 (ddt, J=14.4, 7.2, 4.9 Hz, 1H), 1.97-1.87 (m, 1H), 1.44-1.28 (m, 2H); $^{13}$C NMR (126 MHz, CDCl$_3$) δ 130.41, 128.01, 72.34, 71.76, 70.18, 61.22, 60.69, 48.03, 34.45, 32.35, 22.88, 22.72; HRMS (ESI) calcd. for C$_{12}$H$_{24}$NO$_3$ [M+H]$^+$: 230.1751, found: 230.1753.

Example 16—Preparation of (Z)-3-(2-(2-hydroxyethoxy)ethyl)-3,3a,4,5,9,9a-hexahydrocycloocta[d]oxazol-2(8H)-one (39)

(Z)-8-((2-(2-hydroxyethoxy)ethyl)amino)cycloct-4-enol (12.9 g, 56 mmol, 1.0 equiv) and N,N'-disuccinimidyl carbonate (15.1 g, 59 mmol, 1.05 equiv) were mixed and then acetonitrile (20 mL) was added. The mixture was cooled in ice bath and Et$_3$N (12.5 g, 124 mmol, 2.2 equiv) was added in three portions, which gave a homogenous solution. Upon stirring the solution overnight, a white precipitate formed. To the reaction mixture was added Et$_2$O (100 mL). After cooling to 5° C., the precipitate was filtered off and discarded. The filtrate was concentrated and purified on REDISEP® Gold silica gel column (80 g, 20 mL/min flow rate) by flash chromatography using a gradient from 1 to 5% MeOH in DCM over 25 minutes. Upon solvent removal, pure (Z)-3-(2-(2-hydroxyethoxy)ethyl)-3,3a,4,5,9,9a-hexahydrocycloocta[d]oxazol-2(8H)-one (13.2 g, 92%) was obtained as a viscous oil.

$^1$H (500 MHz, CDCl$_3$) δ 5.82-5.53 (m, 2H), 4.31 (dddd, J=12.4, 8.6, 3.9, 1.4 Hz, 1H), 3.72 (ddt, J=19.0, 8.1, 4.3 Hz, 3H), 3.67-3.49 (m, 5H), 3.24 (dddd, J=14.6, 5.9, 4.2, 1.4 Hz, 1H), 2.44-2.05 (m, 6H), 1.72-1.51 (m, 1H), 1.40-1.31 (m, 1H); $^{13}$C NMR (126 MHz, CDCl$_3$) δ 157.91, 129.71, 129.07, 80.07, 72.32, 68.60, 61.75, 61.17, 41.48, 31.65, 29.25, 21.66, 21.01; HRMS (ESI) calcd. for C$_{13}$H$_{21}$NNaO$_4$ [M+H]$^+$: 278.1363, found: 278.1 374.

Example 17—Preparation of (E)-2((5,8-dihydro-4H-1,3-dioxocin-5-yl)oxy)ethyl(2,5-dioxopyrrolidin-1-yl)carbonate (41)

(E)-2-((5,8-dihydro-4H-1,3-dioxocin-5-yl)oxy)ethanol (261 mg, 1.5 mmol, 1.0 equiv), N,N'-Disuccinimidyl carbonate (769 mg, 3.0 mmol, 2.0 equiv) and triethyl amine (455 mg, 630 μL, 4.5 mmol, 3.0 equiv) were mixed in MeCN (3 mL) under N$_2$ atmosphere and stirred for 5 h in the dark. Solvents were removed at 24° C. under vacuum and then purification of the crude product was performed on a REDISEP® Gold Diol column (50 g) using pentane (10% DCM) to 100% DCM gradient for 40 minutes at a flow rate of 30 mL/min. Removal of the solvent gave 390 mg (83%) of white foam of 95% purity.

$^1$H NMR (500 MHz, CDCl$_3$) δ 6.18 (dd, J=16.3, 11.3 Hz, 1H), 5.90-5.81 (m, 1H), 5.18 (dd, J=8.0, 2.8 Hz, 1H), 4.50 (dt, J=9.3, 3.8 Hz, 2H), 4.44 (dd, J=10.5, 5.8 Hz, 1H), 4.35-4.25 (m, 2H), 4.21 (dd, J=11.2, 6.9 Hz, 1H), 4.01 (td, J=10.1, 2.6 Hz, 1H), 3.92-3.84 (m, 1H), 3.79 (dd, J=11.2, 6.2 Hz, 1H), 3.28-3.20 (m, 1H), 2.90-2.79 (m, 4H); $^{13}$C NMR (101 MHz, CDCl$_3$) δ 168.50, 151.61, 138.00, 136.66, 98.37, 83.57, 77.08, 73.27, 69.80, 67.20, 25.42; HRMS (ESI) calcd. for C$_{13}$H$_{18}$NO$_8$ [M+H]$^+$: 316.1027, found: 319.1035; calcd. for C$_{13}$H$_{21}$N$_2$O$_8$ [M+NH$_4$]$^+$: 333.1292, found: 333.1300.

Example 18—Preparation of (E)-2,5-dioxopyrrolidin-1-yl-(8-(2-(2-(2-methoxyethoxy)ethoxy)ethoxy)cycloct-4-en-1-yl) carbonate (42)

(E)-8-(2-(2-(2-methoxyethoxy)ethoxy)ethoxy)cycloct-4-enol (1440 mg, 5.0 mmol, 1.0 equiv), N,N'-disuccinimidyl carbonate (1538 mg, 6.0 mmol, 1.2 equiv) and triethyl amine (880 mg, 1200 μL, 8.75 mmol, 1.75 equiv) were mixed in MeCN (5 mL) under N$_2$ atmosphere and stirred for two and a half days in the dark. Et$_2$O (20 mL) was added to the reaction mixture and the precipitate was filtered and washed with DCM (2 mL). From the filtrate the solvents were removed at 24° C. under vacuum and then purification of the crude product was performed on a REDISEP® Gold silica gel flash column (80 g) using DCM (1% MeOH) to DCM (4% MeOH) gradient for 25 minutes at a flow rate of 60 mL/min.

Three fractions were collected: 300 mg of first NHS-carbonate, 500 mg of mixture of isomeric NHS-carbonates and 800 mg of starting material. The mixture could be separated on a 40 g REDISEP® Gold silica column using a DCM (0.5% MeOH) to DCM (6.5% MeOH) gradient at a flow rate of 35 mL/min for 19 minutes. This gave 270 mg more of the first isomer and 200 mg of the second. 37%.

First Isomer:
$^1$H NMR (400 MHz, CDCl$_3$) δ 5.62-5.55 (m, 2H), 5.14 (dd, J=9.0, 4.2 Hz, 1H), 4.97 (td, J=8.9, 3.5 Hz, 1H), 3.98 (dd, J=9.0, 5.4 Hz, 1H), 3.73 (dd, J=10.7, 5.7 Hz, 1H), 3.72-3.58 (m, 7H), 3.57-3.51 (m, 2H), 3.48 (dt, J=9.9, 4.8 Hz, 1H) 3.36 (s, 3H), 2.81 (s, 4H), 2.50-2.35 (m, 1H), 2.29-2.06 (m, 4H), 2.05-1.93 (m, 1H), 1.93-1.80 (m, 1H), 1.80-1.70 (m, 1H); $^{13}$C NMR (101 MHz, CDCl$_3$) δ 168.59, 151.01, 133.79, 133.20, 79.63, 76.01, 71.89, 70.73, 70.71, 70.65, 70.53, 68.99, 58.96, 33.12, 31.92, 28.00, 27.82, 25.42; calcd. for C$_{20}$H$_{35}$N$_2$O$_9$ [M+NH$_4$]$^+$: 447.2337, found: 447.2362.

Second Isomer:
$^1$H NMR (400 MHz, CDCl$_3$) δ 5.52 (ddd, J=10.2, 8.8, 3.4 Hz, 2H), 4.61 (ddd, J=11.2, 4.8, 1.5 Hz, 1H), 3.82-3.73 (m, 2H), 3.73-3.62 (m, 8H), 3.58-3.54 (m, 2H), 3.43 (dt, J=8.4, 4.4 Hz, 1H), 3.38 (s, 3H), 2.81 (s, 4H), 2.52-2.41 (m, 1H), 2.41-2.16 (m, 4H), 2.11-1.99 (m, 3H); $^{13}$C NMR (101 MHz, CDCl$_3$) δ 168.80, 151.40, 133.68, 132.22, 85.83, 84.51, 77.20, 72.03, 71.94, 70.61, 70.43, 59.01, 38.82, 37.90, 32.64, 32.22, 25.47; calcd. for C$_{20}$H$_{35}$N$_2$O$_9$ (M+NH$_4$]; 447.2337, found: 447.2345.

Example 19—Preparation of (E)-2,5-dioxopyrrolidin-1-yl-(2-(2-(2-oxo-4,5,9,9a-tetrahydrocycloocta[d]oxazol-3(2H,3aH,8H)-yl)ethoxy)ethyl) carbonate (43)

(E)-3-(2-(2-hydroxyethoxy)ethyl)-3,3a,4,5,9,9a-hexahydrocycloocta[d]oxazol-2(8H)-one (510 mg, 2.0 mmol, 1.0 equiv), N,N'-disuccinimidyl carbonate (615 mg, 2.4 mmol, 1.2 equiv) and triethyl amine (354 mg, 490 μL, 3.5 mmol, 1.75 equiv) were mixed in MeCN (3 mL) under N$_2$ atmosphere and stirred for 3.5 h in the dark. Solvents were removed at 24° C. under vacuum and then purification of the crude product was performed on a silica column (24 g) using DCM (0.5% MeOH) to DCM (3% MeOH) gradient for about 19 minutes at a flow rate of 25 mL/min. Removal of the solvent gave 560 mg (71%) of white foam. The first fractions contained enhanced quantity of the major isomer.

$^1$H NMR (400 MHz, CDCl$_3$) δ 5.99-5.81 (m, 1H), 5.70-5.42 (m, 6H), 4.53-4.40 (m, 6H), 4.26 (t, J=9.6 Hz, 1H), 4.15 (dd, J=10.7, 6.5 Hz, 3H), 3.84-3.50 (m, 20H), 3.32-3.21 (m, 3H), 2.85 (s, 14H), 2.73 (s, 1H), 2.53 (dt, J=15.8, 8.1 Hz, 1H), 2.48-2.15 (m, 18H), 1.97 (apparent qd, J=11.9, 5.2 Hz, 3H), 1.80 (dt, J=21.9, 10.6 Hz, 1H), 1.72-1.48 (m, 6H); $^{13}$C NMR (101 MHz, CDCl$_3$) δ 168.45, 157.07, 151.66, 134.33, 132.81, 83.75, 70.09, 69.35, 68.12, 65.42, 41.79, 38.39, 34.73, 31.96, 31.95, 25.46; calcd. For C$_{18}$H$_{25}$N$_2$O$_8$ [M+H]$^+$: 397.1605, found: 397.1597.

Example 20—Preparation of AZD2281-DO-TCO (45)

4-[[4-Fluoro-3-(4-(N-(2-aminoethyl}-5-oxo-pentanamide)piperazine-1-carbonyl) phenyl]methyl]-2H-phthalazin-1-one (7.4 mg, 14.06 μmol, 1.0 equiv) was dissolved in DMF (300 μL) and triethyl amine (4.2 mg, 5.8 μL, 42.18 μmol, 3.0 equiv) was added. Then (E)-2-((5,8-dihydro-4H-1,3-dioxocin-5-yl)oxy)ethyl-(2,5-dioxopyrrolidin-1-yl) carbonate (5.4 mg, 17.02 μmol, 1.2 equiv) in DCM (2×100 μL) was added to the mixture. The reaction was run for 30 minutes in the dark and then the crude mixture was directly loaded on a BIOTAGE® SNAP 10 g KP-C18-HS cartridge and purified using a water (5% MeCN) to water (95% MeCN) gradient during 20 min at 15 mL/min flow rate. Lyophilization gave 5.4 mg (54%) of white powder.

$^1$H NMR (400 MHz, CDCl$_3$) δ 8.47 (d, J=7.9 Hz, 1H), 7.87-7.69 (m, 3H), 7.39-7.29 (m, 2H), 7.07 (t, J=8.8 Hz, 1H), 6.26 (s, 1H), 6.16 (ddd, J=16.0, 10.5, 3.3 Hz, 1H), 5.82 (dd, J=16.7, 9.2 Hz, 1H), 5.19 (d, J=8.1 Hz, 1H), 4.50 (dd, J=9.6, 3.5 Hz, 1H), 4.29 (s, 2H), 4.29-4.16 (m, 4H), 3.99 (t, J=10.1 Hz, 1H), 3.85-3.75 (m, 3H), 3.75-3.65 (m, 3H), 3.60-3.45 (m, 3H), 3.45-3.30 (m, 6H), 3.25-3.17 (m, 1H), 2.46 (t, J=6.9 Hz, 1H), 2.44-2.34 (m, 1H), 2.29 (t, J=6.5 Hz, 2H), 1.97 (td, J=14.1, 13.4, 6.5 Hz, 2H); calcd. for C$_{36}$H$_{44}$FN$_6$O$_9$ [M+H]$^+$: 723.3148, found: 723.3163.

Example 21—Preparation of AZD2281-3PEGMe-TCO (46)

4-[[4-Fluoro-3-(4-(N-(2-aminoethyl)-5-oxo-pentanamide)piperazine-1-carbonyl) phenyl]methyl]-2H-phthalazin-1-one (7.4 mg, 14.06 μmol, 1.0 equiv) was dissolved in DMF (300 μL) and triethyl amine (4.2 mg, 5.8 μL, 42.18 μmol, 3.0 equiv) was added. Then (E)-2,5-dioxopyrrolidin-1-yl-(8-(2-(2-(2-methoxyethoxy)ethoxy)ethoxy)cyclooct-4-en-1-yl) carbonate (9.0 mg, 20.96 μmol, 1.5 equiv) in DCM (2×100 μL) was added to the mixture. The reaction was run for 30 minutes in the dark and then the crude mixture was directly loaded on a BIOTAGE® SNAP 10 g KP-C18-HS cartridge and purified applying a water (5% MeCN) to water (95% MeCN) gradient during 20 min at 15 mL/min flow rate. Lyophilization gave 8.3 mg (70%) of white powder.

$^1$H NMR (400 MHz, CDCl$_3$) δ 8.50-8.43 (m, 1H), 7.84-7.69 (m, 3H), 7.33 (dd, J=8.0, 4.9 Hz, 2H), 7.06 (t, J=8.8 Hz, 1H), 5.82-5.59 (m, 1H), 5.50 (ddd, J=15.7, 11.3, 3.2 Hz, 1H), 5.22-5.03 (m, 1H), 4.29 (s, 2H), 3.90 (s, 1H), 3.83-3.74 (m, 3H), 3.74-3.62 (m, 10H), 3.60-3.55 (m, 5H), 3.50 (dd, J=9.7, 4.9 Hz, 1H), 3.39 (broad s, 8H), 2.48 (t, J=7.0 Hz, 1H), 2.41 (t, J=6.8 Hz, 1H), 2.30 (t, J=6.8 Hz, 2H), 2.20-2.09 (m, 2H), 2.06-1.90 (m, 4H), 2.90-1.70 (m, 4H), 1.66 (td, J=14.1, 4.9 Hz, 1H); calcd. for C$_{43}$H$_{58}$FN$_6$O$_{10}$ [M+H]$^+$: 837.4193, found: 837.4195.

Example 22—Preparation of AZD2281-OX-TCO (47)

4-[[4-Fluoro-3-(4-(N-(2-aminoethyl)-5-oxo-pentanamide)piperazine-1-carbonyl) phenyl]methyl]-2H-phthalazin-1-one (7.4 mg, 14.06 μmol, 1.0 equiv) was dissolved in DMF (300 μL) and triethyl amine (4.2 mg, 5.8 μL, 42.18 μmol, 3.0 equiv) was added. Then, (E)-2,5-dioxopyrrolidin-1-yl-(2-(2-(2-oxo-4,5,9,9a-tetrahydrocyclocta[d]oxazol-3(2H,3aH,8H)-yl)ethoxy)ethyl) carbonate (6.8 mg, 17.02 μmol, 1.2 equiv) in DCM (2×100 μL) was added to the mixture. The reaction was stirred for 30 minutes in the dark and then the crude mixture was directly loaded on a BIOTAGE® SNAP 10 g KP-C18-HS cartridge and purified applying a water (5% MeCN) to water (95% MeCN) gradient during 20 min at 15 mL/min flow rate. Lyophilization gave 8.3 mg (74%) of white powder.

$^1$H NMR (400 MHz, CDCl$_3$) 8.46 (dd, J=7.3, 2.5 Hz, 1H), 7.87-7.68 (m, 3H), 7.33 (t, J=6.1 Hz, 2H), 7.06 (t, J=8.9 Hz, 1H), 5.64-5.44 (m, 2H), 4.29 (s, 2H), 4.27-4.23 (m, 1H), 4.16 (dd, J=11.3, 6.4 Hz, 2H), 3.86-3.48 (m, 13H), 3.42-3.11 (m, 8H), 2.51-2.33 (m, 4H), 2.34-2.17 (m, 5H), 2.06-1.88 (m, 3H); calcd. for C$_{41}$H$_{51}$FN$_7$O$_9$ [M+H]$^+$: 804.3727, found: 804.3730.

Example 23—Tetrazine Kinetics with Cyclooctenes

Kinetic measurements were performed with benzylamino tetrazine and excessive amounts of cyclooctenes, using an Applied Photophysics Stopped-Flow spectrophotometer. Stock solutions of reactants in DMSO were diluted in PBS pH 7.4 to a final concentration of 1 vol % DMSO. Solutions of these reactants were loaded into the individual chambers of the instrument and equilibrated to 37° C. for 10 min. The concentration of benzylamino tetrazine after the samples were mixed by the spectrometer in a 1:1 v/v ratio was 50, 75 or 150 μM depending on the cyclooctene used. The decrease of the benzylamino tetrazine absorbance measured at 515 nm was monitored at regular intervals between 0.075 s and 10 s depending on the cyclooctene used. For trials shorter than 1s (TCO-OH, OX-TCO and 3PEGMe-TCO) 1000 data points were collected and for trials longer than 1 s (EG-TCO and DO-TCO) 10000 data points were collected. Measurements were performed at five different concentrations for each cyclooctene as shown in Table 7.

The $k_{obs}$ (s$^{-1}$) values were calculated using the Prism 6 software package and the results of 6 runs were averaged for each cyclooctene concentration. The average $k_{obs}$ values were then plotted against the concentration of cyclooctenes to yield the second order rate constant. The average $k_{obs}$ values were then plotted against the concentration of cyclooctenes to yield the second order rate constant $k_2$=(dm$^3$ mol$^{-1}$ s$^{-1}$) from the slope of the line with the error from the standard deviation in the slope calculated in Prism 6.

TABLE 7

Experimental setup and the second rate constants for the reaction of cyclooctenes with benzylamino tetrazyne in PBS at 37° C.

| Cyclooctene | $C_{cyclooctene}$ (mM) | $C_{tetra}$ (μM) | Run time (s) | $n^a$ | $k_2$ $(dm^3 \cdot mol^{-1} \cdot s^{-1})$ |
|---|---|---|---|---|---|
| TCO | 1.42, 1.65, 1.89, 2.13, 2.36 | 75 | 0.15 | 1000 | 33585 ± 326 |
| EG-TCO | 2.57, 3.00, 3.43, 3.86, 4.23 | 150 | 6 | 10000 | 600 ± 6 |
| DO-TCO | 2.57, 3.00, 3.43, 3.86, 4.23 | 150 | 10 | 10000 | 332 ± 3 |
| OX-TCO | 1.2, 1.4, 1.6, 1.8, 2.6 | 50 | 0.175 | 1000 | 29242 ± 636 |
| 3PEGMe-TCO$_A$ | 0.90, 1.16, 1.55, 1.93, 2.71 | 75 | 0.2 | 1000 | 20643 ± 387 |
| 3PEGMe-TCO$_B$ | 0.81, 1.04, 1.39, 1.74, 2.43 | 75 | 0.075 | 1000 | 108041 ± 2481 |

$^a$number of data points collected.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I:

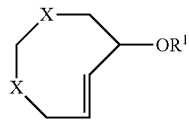

or a pharmaceutically acceptable salt thereof,
wherein:
  each X is independently $CH_2$ or O;
  $R^1$ is $(CH_2—CH_2—O)_nR^2$;
  $R^2$ is selected from the group consisting of H, $C_{1-6}$alkyl, and an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester; and
  n is an integer from 1 to 20.

2. The compound of claim 1, wherein the compound of Formula I is a compound of Formula IA:

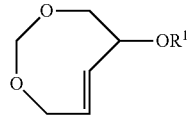

or a pharmaceutically acceptable salt thereof,
wherein:
  $R^1$ is $(CH_2—CH_2—O)_nR^2$;
  $R^2$ is selected from the group consisting of H, $C_{1-6}$alkyl, or an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester; and
  n is an integer from 1 to 20.

3. The compound of claim 1, wherein $R^2$ is selected from H and $C_{1-6}$alkyl.

4. The compound of claim 1, wherein $R^2$ is an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester.

5. The compound of claim 4, wherein $R^2$ is an NHS ester which is an NHS carbamate.

6. The compound of claim 5, wherein the NHS carbamate is N,N'-disuccinimidyl carbonate.

7. The compound of claim 1, wherein n is 1.

8. The compound of claim 1, wherein the compound of Formula I is selected from the group consisting of:

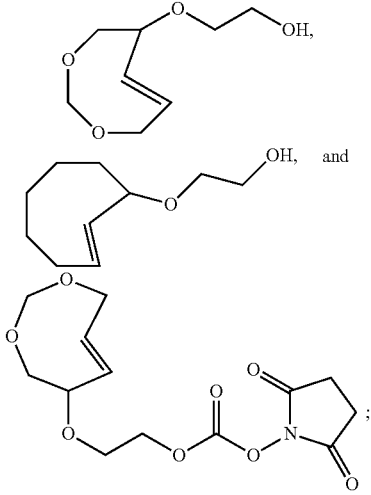

or a pharmaceutically acceptable salt thereof.

9. A compound of Formula II:

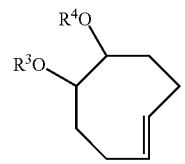

or a pharmaceutically acceptable salt thereof,
wherein:
  $R^3$ is selected from the group consisting of H, $C_{1-6}$alkyl, and $—(CH_2—CH_2—O)_nR^5$;

R[4] is selected from the group consisting of H, C$_{1-6}$alkyl, and —(CH$_2$—CH$_2$—O)$_n$R[5];

wherein one of R[3] and R[4] is —(CH$_2$—CH$_2$—O)$_n$R[5];

R[5] is selected from the group consisting of H, C$_{1-6}$alkyl, and an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester; and n is an integer from 1 to 20.

10. The compound of claim 9, wherein R[3] is H.

11. The compound of claim 9, wherein R[5] is a C$_{1-6}$alkyl.

12. The compound of claim 9, wherein R[5] is an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester.

13. The compound of claim 12, wherein R[5] is an NHS ester which is an NHS carbamate.

14. The compound of claim 13, wherein the NHS carbamate is N,N'-disuccinimidyl carbonate.

15. The compound of claim 9, wherein n is 3.

16. The compound of claim 9, wherein the compound of Formula II is selected from the group consisting of:

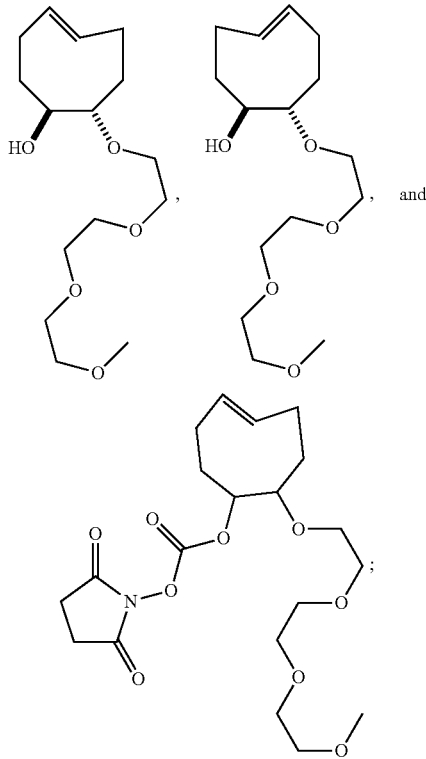

or a pharmaceutically acceptable salt thereof.

17. A compound of Formula III:

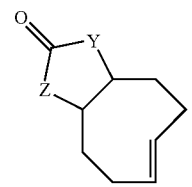

or a pharmaceutically acceptable salt thereof,
wherein:
Y is O or NR[6];
Z is O or NR[6];
wherein one of Y and Z is O, and the other is NR[6];
R[6] is —(CH$_2$)$_m$—(CH$_2$—CH$_2$—O)$_n$R[7];
R[7] is selected from the group consisting of H, C$_{1-6}$alkyl, and an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester;
m is an integer from 1 to 20; and
n is an integer from 1 to 20.

18. The compound of claim 17, wherein R[7] is a H.

19. The compound of claim 17, wherein R[7] is an amine-reactive crosslinking group selected from the group consisting of an isothiocyanate, an isocyanate, an acyl azide, an NHS ester, a sulfonyl chloride, an aldehyde, a glyoxal, an epoxide, an oxirane, a carbonate, an aryl halide, an imidoester, a carbodiimide, an anhydride, a hydrazine, a hydrazide, a hydroxyl amine, and a fluorophenyl ester.

20. The compound of claim 19, wherein R[7] is an NHS ester which is an NHS carbamate.

21. The compound of claim 20, wherein the NHS carbamate is N,N'-disuccinimidyl carbonate.

22. The compound of claim 17, wherein n is 1.

23. The compound of claim 17, wherein m is 2.

24. The compound of claim 17, wherein the compound of Formula III is selected from the group consisting of:

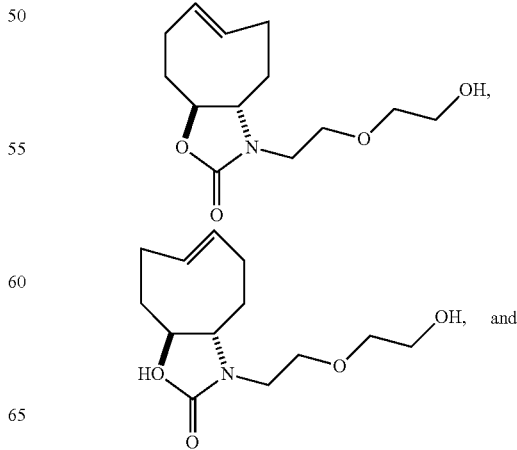

-continued
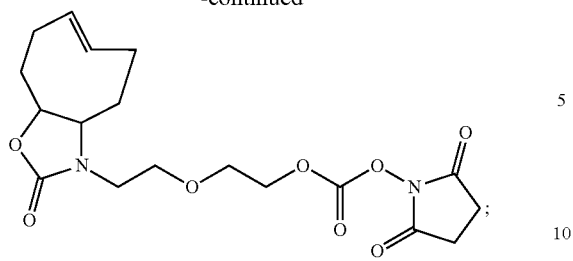
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 10,179,775 B2 | |
| APPLICATION NO. | : 15/502806 | |
| DATED | : January 15, 2019 | |
| INVENTOR(S) | : Scott A. Hilderbrand, Balazs R. Varga and Ralph Weissleder | |

It is certified that error appears in the above-identified patent and that said Letters Patent is hereby corrected as shown below:

On the Title Page

Column 1 (Title) Line 1 (approx.), delete "BIOORTHOGONOL" and insert
-- BIOORTHOGONAL --, In the Specification In Column 1, Line 1, delete "BIOORTHOGONOL" and insert -- BIOORTHOGONAL --, In the Claims In Column 39, Line 47, Claim 1, delete "$(CH_2-CH_2-O)_nR^2$;" and insert
-- $-(CH_2-CH_2-O)_nR^2$; --, In Column 40, Line 2, Claim 2, delete "$(CH_2-CH_2-O)_nR^2$;" and insert
-- $-(CH_2-CH_2-O)_nR^2$; --.

Signed and Sealed this
Twentieth Day of October, 2020

Andrei Iancu
*Director of the United States Patent and Trademark Office*